US011229790B2

(12) United States Patent
Errico et al.

(10) Patent No.: US 11,229,790 B2
(45) Date of Patent: Jan. 25, 2022

(54) MOBILE PHONE FOR TREATING A PATIENT WITH SEIZURES

(71) Applicant: ElectroCore, LLC, Basking Ridge, NJ (US)

(72) Inventors: Joseph P. Errico, Warren, NJ (US); Steven Mendez, Chester, NJ (US); Bruce J. Simon, Mountain Lakes, NJ (US)

(73) Assignee: electroCore, Inc., Rockaway, NJ (US)

( * ) Notice: Subject to any disclaimer, the term of this patent is extended or adjusted under 35 U.S.C. 154(b) by 1025 days.

(21) Appl. No.: 14/335,726

(22) Filed: Jul. 18, 2014

(65) Prior Publication Data

US 2014/0330334 A1 Nov. 6, 2014

Related U.S. Application Data

(63) Continuation-in-part of application No. 14/292,491, filed on May 30, 2014, now Pat. No. 9,375,571, and
(Continued)

(51) Int. Cl.
*A61N 1/36* (2006.01)
*A61N 1/04* (2006.01)
(Continued)

(52) U.S. Cl.
CPC ........ *A61N 1/36025* (2013.01); *A61B 5/4094* (2013.01); *A61B 5/4836* (2013.01);
(Continued)

(58) Field of Classification Search
None
See application file for complete search history.

(56) References Cited

U.S. PATENT DOCUMENTS 3,590,810 A 7/1971 Kopecky
4,196,737 A 4/1980 Bevilacqua
(Continued)

FOREIGN PATENT DOCUMENTS

EP 1967226 9/2008
EP 2777764 8/2015
(Continued)

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.
(Continued)

*Primary Examiner* — Jennifer Pitrak McDonald
*Assistant Examiner* — Elizabeth K So
(74) *Attorney, Agent, or Firm* — Farber LLC

(57) ABSTRACT

Devices, systems and methods are disclosed that allow a patient to self-treat epileptic seizures by electrical noninvasive stimulation of a vagus nerve. The system comprises a handheld stimulator that is applied to the surface of the patient's neck, wherein the stimulator comprises or is joined to a smartphone. A camera of the smartphone may be used to position and reposition the stimulator to a particular location on the patient's neck. The system may also comprise a base station that is used to meter the charging of a rechargeable battery within the stimulator. The base station and stimulator transmit data to one another regarding the status of a stimulation session.

18 Claims, 13 Drawing Sheets

Related U.S. Application Data a continuation-in-part of application No. 13/858,114, filed on Apr. 8, 2013, now Pat. No. 9,248,286.

(60) Provisional application No. 62/001,004, filed on May 20, 2014, provisional application No. 61/752,895, filed on Jan. 15, 2013.

(51) Int. Cl.

| | | |
|---|---|---|
| A61B 5/00 | (2006.01) | |
| H04M 1/21 | (2006.01) | |
| A61B 5/0205 | (2006.01) | |
| A61B 5/021 | (2006.01) | |
| A61B 5/024 | (2006.01) | |
| A61B 8/00 | (2006.01) | |
| A61B 5/08 | (2006.01) | |
| A61B 5/316 | (2021.01) | |
| A61B 5/332 | (2021.01) | |
| A61B 5/349 | (2021.01) | |
| A61B 5/369 | (2021.01) | |

(52) U.S. Cl.
CPC .......... *A61B 5/6898* (2013.01); *A61N 1/0456* (2013.01); *A61N 1/36034* (2017.08); *H04M 1/21* (2013.01); *A61B 5/021* (2013.01); *A61B 5/0205* (2013.01); *A61B 5/02438* (2013.01); *A61B 5/0816* (2013.01); *A61B 5/316* (2021.01); *A61B 5/332* (2021.01); *A61B 5/349* (2021.01); *A61B 5/369* (2021.01); *A61B 5/681* (2013.01); *A61B 5/6804* (2013.01); *A61B 5/6822* (2013.01); *A61B 5/6843* (2013.01); *A61B 5/7207* (2013.01); *A61B 8/00* (2013.01); *A61B 2505/07* (2013.01); *A61B 2560/0242* (2013.01); *A61B 2562/0219* (2013.01); *A61N 1/36064* (2013.01)

(56) References Cited

U.S. PATENT DOCUMENTS

| | | | |
|---|---|---|---|
| 4,989,605 A | 2/1991 | Rossen | |
| 5,109,847 A | 5/1992 | Liss et al. | |
| 5,458,141 A | 10/1995 | Neil | |
| 5,487,759 A | 1/1996 | Bastyr et al. | |
| 5,782,874 A | 7/1998 | Loos | |
| 5,899,922 A | 5/1999 | Loos | |
| 5,983,131 A | 11/1999 | Weaver et al. | |
| 6,341,236 B1 | 1/2002 | Osorio et al. | |
| 6,366,814 B1 | 4/2002 | Boveja et al. | |
| 6,463,327 B1 | 10/2002 | Lurie et al. | |
| 6,587,719 B1 | 7/2003 | Barrett et al. | |
| 6,610,713 B2 | 8/2003 | Tracey | |
| 6,631,297 B1 | 10/2003 | Mo | |
| 7,734,340 B2 | 6/2010 | De Ridder | |
| 7,797,041 B2 | 9/2010 | Libbus et al. | |
| 8,868,117 B2 | 12/2014 | Simon et al. | |
| 9,248,286 B2* | 2/2016 | Simon ............... A61N 1/36021 | |
| 9,375,571 B2* | 6/2016 | Errico ............... A61N 1/36021 | |
| 2002/0099417 A1 | 7/2002 | Naritoku et al. | |
| 2002/0183237 A1 | 12/2002 | Puskas | |
| 2002/0183804 A1 | 12/2002 | Malaney et al. | |
| 2003/0212311 A1 | 11/2003 | Nova et al. | |
| 2004/0073271 A1 | 4/2004 | Harry et al. | |
| 2004/0122281 A1 | 6/2004 | Fischell et al. | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0113630 A1 | 5/2005 | Fox et al. | |
| 2005/0125044 A1 | 6/2005 | Tracey | |
| 2005/0137644 A1 | 6/2005 | Boveja et al. | |
| 2005/0187590 A1 | 8/2005 | Boveja et al. | |
| 2005/0216062 A1 | 9/2005 | Herbst | |
| 2005/0267544 A1* | 12/2005 | Lee ............... A61N 1/36021 | 607/46 |
| 2006/0015153 A1 | 1/2006 | Gliner et al. | |
| 2006/0074284 A1 | 4/2006 | Juola et al. | |
| 2006/0074450 A1 | 4/2006 | Boveja et al. | |
| 2006/0100668 A1 | 5/2006 | Ben-David et al. | |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2007/0027496 A1 | 2/2007 | Parnis et al. | |
| 2007/0038264 A1 | 2/2007 | Jaax et al. | |
| 2007/0067002 A1 | 3/2007 | Lozano | |
| 2007/0106337 A1 | 5/2007 | Errico et al. | |
| 2007/0123952 A1 | 5/2007 | Strother et al. | |
| 2007/0142886 A1 | 6/2007 | Fischell et al. | |
| 2007/0150006 A1 | 6/2007 | Libbus et al. | |
| 2007/0156182 A1 | 7/2007 | Castel et al. | |
| 2007/0276449 A1 | 11/2007 | Gunter et al. | |
| 2008/0006281 A1 | 1/2008 | Sih et al. | |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0077192 A1 | 3/2008 | Harry et al. | |
| 2008/0114199 A1 | 5/2008 | Riehl et al. | |
| 2008/0132964 A1 | 6/2008 | Cohen et al. | |
| 2008/0177190 A1 | 7/2008 | Libbus et al. | |
| 2008/0208266 A1 | 8/2008 | Lesser et al. | |
| 2008/0249439 A1 | 10/2008 | Lesser et al. | |
| 2008/0306325 A1 | 12/2008 | Burnett et al. | |
| 2009/0112283 A1 | 4/2009 | Kriksunov et al. | |
| 2009/0132018 A1 | 5/2009 | DiUbaldi et al. | |
| 2009/0157149 A1 | 6/2009 | Wahlgren et al. | |
| 2009/0234417 A1 | 9/2009 | Pastena et al. | |
| 2009/0234419 A1 | 9/2009 | Maschino et al. | |
| 2009/0240297 A1 | 9/2009 | Shavit et al. | |
| 2009/0287035 A1 | 11/2009 | Dietrich et al. | |
| 2010/0030299 A1 | 2/2010 | Covalin | |
| 2010/0152794 A1 | 6/2010 | Radivojevic et al. | |
| 2010/0286553 A1 | 11/2010 | Feler et al. | |
| 2011/0046432 A1 | 2/2011 | Simon et al. | |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1 | 9/2011 | Simon et al. | |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |
| 2013/0006322 A1 | 1/2013 | Tai | |
| 2013/0060304 A1 | 3/2013 | LaTendresse et al. | |
| 2013/0204741 A1 | 8/2013 | Underwood | |
| 2013/0245486 A1 | 9/2013 | Simon et al. | |
| 2014/0005743 A1 | 1/2014 | Giuffrida et al. | |
| 2014/0172041 A1* | 6/2014 | Draghici ............... A61N 1/0548 | 607/45 |
| 2014/0222102 A1 | 8/2014 | Lemus et al. | |
| 2015/0165226 A1 | 6/2015 | Simon et al. | |
| 2015/0190637 A1 | 7/2015 | Simon et al. | |

FOREIGN PATENT DOCUMENTS

| | | |
|---|---|---|
| JP | 2009-125263 | 6/2009 |
| JP | 2009233024 | 10/2009 |
| KR | 101242190 | 3/2013 |
| WO | WO1993/01862 | 2/1993 |
| WO | WO 1993/01862 | 2/1993 |
| WO | WO2005/007120 | 1/2005 |
| WO | WO2007/092062 | 8/2007 |
| WO | WO2008/042902 | 4/2008 |
| WO | WO2007/058780 | 5/2008 |
| WO | WO 2009/021080 | 2/2009 |
| WO | WO2009/021080 | 2/2009 |
| WO | WO2009/064641 | 5/2009 |
| WO | WO2009/135693 | 11/2009 |
| WO | WO 2009/135693 | 11/2009 |

(56) References Cited

FOREIGN PATENT DOCUMENTS

| WO | WO2012/121750 | 9/2012 |
|---|---|---|
| WO | WO2013/066135 | 5/2013 |

OTHER PUBLICATIONS

Al-Kaisy et al., Poster, The American Academy of Pain Medicine. Analgeia of axial low back pain with novel spinal neuromodulation. Poster presentation #202 at the 2011 meeting of The American Academy of Pain Medicine, held in National Harbor, MD, 2011.
Albert et al., Deep brain stimulation, vagal nerve stimulation and transcranial stimulation: An overview of stimulation parameters and neurotransmitter release. Neuroscience and Biobehavioral Reviews 2009, 33, pp. 1042-1060.
Amen et al., Peripheral nerve stimulator for the treatment of supraorbital neuralgia: a retrospective case series. Cephalalgia 28, 2008, pp. 355-359.
Andrews, Neuromodulation. I. Techniques-deep brain stimulation, vagus nerve stimulation, and transcranial magnetic stimulation. Ann. N. Y. Acad. Sci. 993, 2003, pp. 1-13.
Asensio-Sampler et al., Peripheral neurostimulation in supraorbital neuralgia refractory to conventional therapy. Pain Pract 8, 2008, pp. 120-124.
Bennetto et al., Trigeminal neuralgia and its management. BMJ 334(7586), 2007, pp. 201-205.
Boinagrov et al., Strength-Duration Relationship for Extracellular Neural Stimulation: Numerical and Analytical Models. J Neurophysiol 104 2010, pp. 2236-2248.
Buchman, Nonlinear dynamics, complex systems, and the pathobiology of critical illness. Curr Opin Crit Care 10, 2004, pp. 378-382.
Cefaly Device, Food and Drug Administration Submission No. K122566, Transcutaneous Electrical Nerve Stimulator to Treat Headache, Dec. 2012 (15 pages).
Conder et al., Android Wireless Application Development, Second Edition. Upper Saddle River, NJ: Addison-Wesley, 2011.
Conway et al., Cerebral blood flow changes during vagus nerve stimulation for depression. Psychiatry Res. 146, 2006, pp. 179-184.
Cruccu et al., Unmyelinated trigeminal pathways as assessed by laser stimuli in humans. Brain 126, 2003, (Pt. 10), pp. 2246-2256.
Datta et al., Transcranial current stimulation focality using disc and ring electrode configurations: FEM analysis. J. Neural Eng. 5, 2008, pp. 163-174.
Delitto et al., Electrical stimulation of the quadriceps femoris in an elite weight lifter: a single subject experiment. Int J Sports Med 10, 1989, pp. 187-191.
Dimarzio, Android—A Programmer's Guide. New York: McGraw-Hill, 2008, pp. 1-319.
Evans et al., Intraoperative human vagus nerve compound action potentials. Acta Neurol Scand 110, 2004, pp. 232-238.
Falluco et al., The anatomical morphology of the supraorbital notch: clinical relevance to the surgical treatment of migraine headaches. Plast Reconstr Surg 130, 2012, pp. 1227-1233.
George et al., Noninvasive techniques for probing neurocircuitry and treating illness: vagus nerve stimulation (VNS), transcranial magnetic stimulation (TMS) and transcranial direct current stimulation (tDCS). Neuropsychopharmacology 35, 2010, pp. 301-316.
Gerardy et al., A pilot study on supra-orbital surface electrotherapy in migraine. Cephalalgia 29, 2009, 134 (poster session).
Grill et al., Stimulus waveforms for selective neural stimulation. IEEE Eng. Med. Biol. 14, 1995, pp. 375-385.
Groves et al., Vagal nerve stimulation: a review of its applications and potential mechanisms that mediate its clinical effects, Neurosci Biobehav Rev 29, 2005, pp. 493-500.
Hennings, Selective Electrical Stimulation of Peripheral Nerve Fibers: Accommodation Based Methods. Ph.D. Thesis, Center for Sensory-Motor Interaction, Aalborg University, Aalborg, Denmark, 2004.
Huston et al., Transcutaneous vagus nerve stimulation reduces serum high mobility group box 1 levels and improves survival in murine sepsis. Crit Care Med35, 2007, pp. 2762-2768.
Janis et al., Anatomy of the supratrochlear nerve: implications for the surgical treatment of migraine headaches. Plast Reconstr Surg 131, 2013, pp. 743-750.
Jasper et al., Implanted occipital nerve stimulators. Pain Physician 11, 2008, pp. 187-200.
Jenkins et al., Neurostimulation for primary headache disorders, part 1: pathophysiology and anatomy, history of neuromodulation in headache treatment, and review of peripheral neuromodulation in primary headaches. Headache 51, 2011, pp. 1254-1266.
Johnson et al., Analgesic effects of different pulse patterns of transcutaneous electrical nerve stimulation on cold-induced pain in normal subjects, Journal of Psychosomatic Research 35, 1991, pp. 313-321.
JP2009233024, Published Oct. 15, 2009, Abstract in English, downloaded from espacenet (2 pages).
Jurgens et al., Pearls and pitfalls: neurostimulation in headache. Cephalalgia 33, 2013, pp. 512-525.
Keller et al., Electrodes for transcutaneous (surface) electrical stimulation. Journal of Automatic Control, University of Belgrade 18, 2008, pp. 35-45.
Kraus et al., BOLD fMRI deactivation of limbic and temporal brain structures and mood enhancing effect by transcutaneous vagus nerve stimulation. J Neural Transm114, 2007, pp. 1485-1493.
Labiner et al., Vagus nerve stimulation therapy in depression and epilepsy: therapeutic parameter settings. Acta. Neurol. Scand. 115, 2007, pp. 23-33.
Lambru et al., Peripheral neurostimulation in primary headaches. Neurological Sciences 35, 2014, pp. 77-81.
Laufer et al., Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88, 2008, pp. 1167-1176.
Li et al., Patents, software and hardware for PID control: an overview and analysis of the current art. IEEE Control Systems Magazine, 26, 2006, pp. 42-54.
Magis et al., Advances and challenges in neurostimulation for headaches. Lancet Neurol 11, 2012, pp. 708-719.
Magis et al., Safety and patients' satisfaction of transcutaneous Supraorbital NeuroStimulation (tSNS) with the Cefaly® device in headache treatment: a survey of 2,313 headache sufferers in the general population, J Headache Pain, 1, 2013, pp. 1-8.
Mapstone, Vagus nerve stimulation: current concepts. Neurosurg Focus 25, 3rd edition, 2008, E9, pp. 1-4.
Moore, Electrical Stimulation for pain suppression: mathematical and physical models. Thesis, School of Engineering, Cornell University, 2007.
Narouze et al., Supraorbital nerve electric stimulation for the treatment of intractable chronic cluster headache: a case report. Headache 47, 2007, pp. 1100-1102.
Perlmutter et al., Deep brain stimulation. Annu. Rev. Neurosci 29, 2006, pp. 229-257.
Petrofsky et al., The transfer of current through skin and muscle during electrical stimulation with sine, square, Russian and interferential waveforms. Journal of Medical Engineering and Technology 33, 2009, pp. 170-181.
Piquet et al., Supraorbital transcutaneous neurostimulation has sedative effects in healthy subjects. BMC Neurol 11, 2011, pp. 1-7.
Rasskazoff et al., Neuromodulation for cephalgias. Surg Neurol Int., 2013, Suppl. 3; S136-S150.
Rattay, Analysis of models for extracellular fiber stimulation. IEEE Trans. Biomed. Eng. 36, 1989, pp. 676-682.
Rattay, The basic mechanism for the electrical stimulation of the nervous system. Neuroscience 89, 1999, pp. 335-346.
Reilly, Electrical models for neural excitation studies. Johns Hopkins APL Technical Digest 9, 1988, pp. 44-59.
Samsung Mobile SDK, Overview, http://developer.samsung.com/samsung-mobile-sdk (1 page).
Sawicki et al., Mathematical Modelling of Vagus Nerve Stimulation. Krawczyk, A. Electromagnetic Field, Health and Environment: Proceedings of EHE'07. Amsterdam, IOS Press, 2008, pp. 92-97.

(56) References Cited

OTHER PUBLICATIONS

Schoenen et al., Migraine prevention with a supraorbital transcutaneous stimulator: a randomized controlled trial. Neurology 80, 2013, pp. 697-704.
Schwarz et al., The Android Developer's Cookbook. Building Applications with the Android SDK, Second Edition. Upper Saddle River, NJ: Addison-Wesley, 2013.
Schwedt, Neurostimulation for Primary Headache Disorders. Curr Neurol Neurosci Rep 9, 2009, pp. 101-107.
Sein et al., Peripheral nerve stimulator placement with ultrasound guidance for the treatment of intractable postherpetic neuralgia: A case report., Poster 267, Proceedings of the17th Annual Meeting of the North American Neuromodulation Society. Las Vegas, Nevada, USA 20, 2013.
Silberstein, Migraine. LANCET 363, 2004, pp. 381-391.
Simopoulos et al., Implanted auriculotemporal nerve stimulator for the treatment of refractory chronic migraine. Headache 50, 2010, pp. 1064-1069.
Slavin et al., Trigeminal and occipital peripheral nerve stimulation for craniofacial pain: a single-institution experience and review of the literature. Neurosurg Focus 21, 2006, E6, pp. 1-5.
Spinner et al., Accuracy of ultrasound-guided superficial trigeminal nerve blocks using methylene blue in cadavers. Pain Med 13, 2012, pp. 1469-1473.
Swett et al., Electrical stimulation of peripheral nerve. Electrical Stimulation Research Techniques, Michael M. Patterson and Raymond P. Kesner, eds. Academic Press. New York, 1981, pp. 243-295.
Terry, Jr., Vagus nerve stimulation: a proven therapy for treatment of epilepsy strives to improve efficacy and expand applications. Conf Proc IEEE Eng Med Biol Soc., 2009, 4631-4634.
Vaisman et al., The treatment of medically intractable trigeminal autonomic cephalalgia with supraorbital/supratrochlear stimulation: a retrospective case series. Neuromodulation 15, 2012. pp. 374-380.
Vargas et al., The Face of Chronic Migraine: Epidemiology, Demographics, and Treatment Strategies. Neurol Clin 27, 2009, pp. 467-479.
Vuckovic et al., A comparative study of three techniques for diameter selective fiber activation in the vagal nerve: anodal block, depolarizing prepulses and slowly rising pulses. J. Neural Eng. 5, 2008, pp. 275-286.
Vuckovic et al., Different Pulse Shapes to Obtain Small Fiber Selective Activation by Anodal Blocking—A Simulation Study. IEEE Transactions on Biomedical Engineering 51, 2004, pp. 698-706.
Ward, Electrical Stimulation Using Kilohertz-Frequency Alternating Current. Physical Therapy 89, 2009, pp. 181-190.
Ward et al., Russian Electrical Stimulation: The Early Experiments. Physical Therapy 82, 2002, pp. 1019-1030.
White et al., Electroanalgesia: Its Role in Acute and Chronic Pain Management. Anesth Analg 92, 2001, pp. 505-513.
Wolfson, Android Developer Tools Essentials. Sebastopol, California: O'Reilly Media Inc., 2013.
Europe Office Action dated Jul. 26, 2018 in related Application No. 11818591.7 filed Aug. 12, 2011 (8 pages).
Europe Office Action dated Apr. 24, 2018 in related Application No. 15796247.3 filed May 20, 2015 (6 pages).
International Search Report and Written Opinion dated Aug. 25, 2015 in related Application No. PCT/US15/31847 filed May 20, 2015 (10 pages).
KR101242190 dated Mar. 25, 2013, Espacenet computer generated English translation (11 pages).
International Search Report and Written Opinion dated May 8, 2007 in related PCT Application No. PCT/US2006/042823 filed Nov. 2, 2006 (5 pages).
International Search Report and Written Opinion dated Sep. 17, 2007 in related PCT Application No. PCT/US2006/042828 filed Nov. 2, 2006 (5 pages).
International Search Report and Written Opinion dated Mar. 26, 2008 in related PCT Application No. PCT/US2006/042752 filed Nov. 1, 2006 (7 pages).
International Search Report and Written Opinion dated Dec. 22, 2011 in related PCT Application No. PCT/US2011/049844 filed Aug. 31, 2011 (9 pages).
International Search Report and Written Opinion dated Apr. 30, 2013 in related PCT Application No. PCT/US2013/023014 filed Jan. 24, 2013 (7 pages).
International Search Report and Written Opinion dated Dec. 11, 2013 in related PCT Application No. PCT/US2013/058079 filed Sep. 4, 2013 (8 pages).
International Search Report and Written Opinion dated Jan. 29, 2014 in related PCT Application No. PCT/US2013/068804 filed Nov. 6, 2013 (10 pages).
Greicius et al., Functional connectivity in the resting brain: A network analysis of the default mode hypothesis, PNAS, Jan. 2003, vol. 100, No. 1, pp. 253-258.
Lee et al., Clustering of Resting State Networks, PLoS One, Jul. 2012, vol. 7, Issue 7, pp. 1-12.
Miyoshi, K. and Morimura, Y. "Clinical Manifestations of Neuropsychiatric Disorders," 2010, Neuropsychiatric Disorders, Springer, XIV, pp. 1-15.
Mucida et al., Reciprocal TH17 and regulatory T cell differentiation mediated retinoic acid, Science, Jul. 13, 2007;317(5835):256-60.
Nozaki et al., Anti-inflammatory effect of all-trans-retinoic acid in inflammatory arthritis. Clin. Immunol. Jun. 2006;119(3):272-9.
Pavlov et al., The cholinergic anti-inflammatory pathway: a missing link in neuroimmunomodulation. Mol Med. May-Aug. 2003;9(5-8):125-34.

* cited by examiner

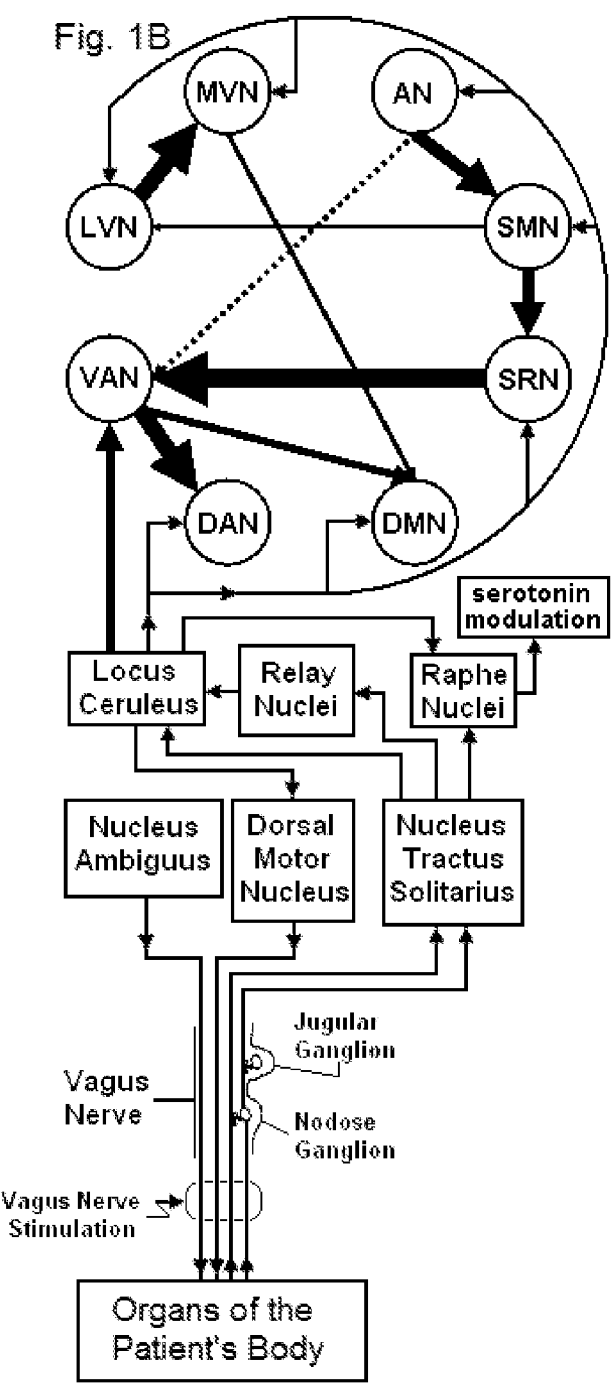

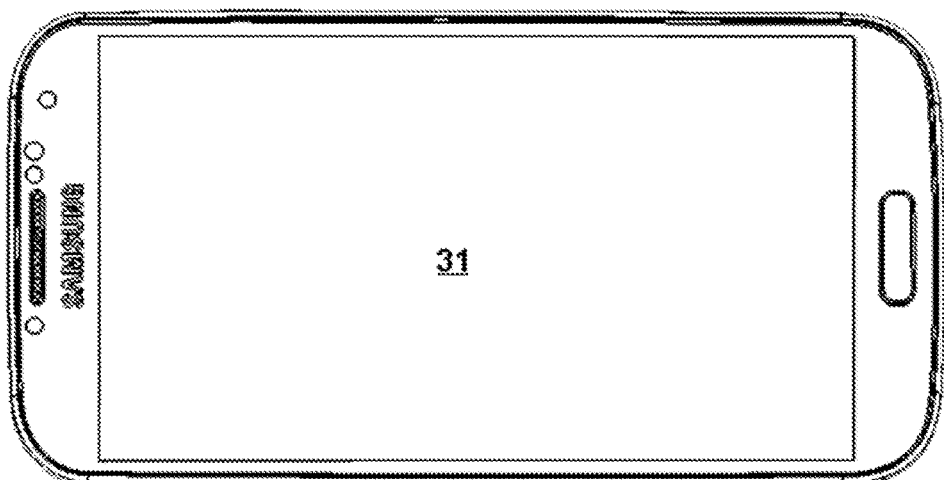
FIG. 3A FRONT VIEW
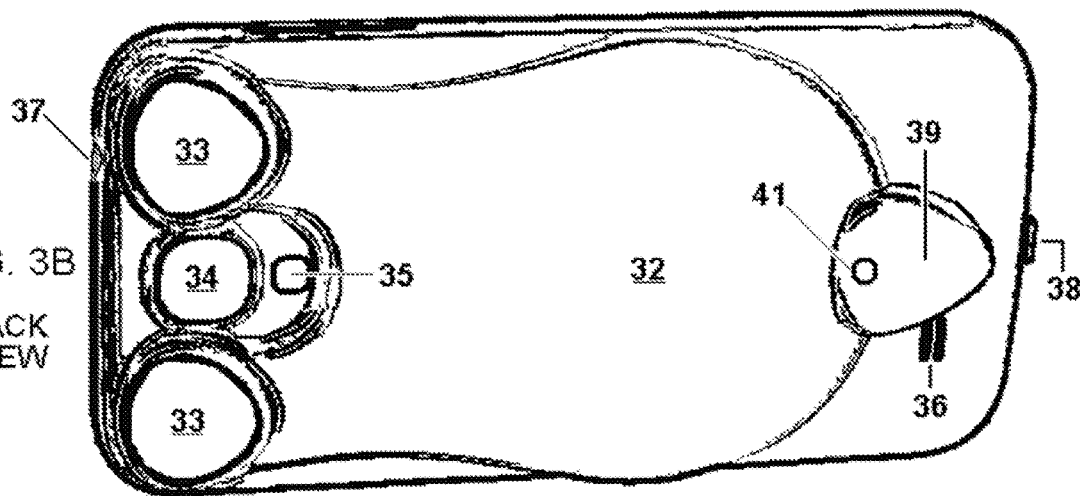
FIG. 3B BACK VIEW
FIG. 3C SIDE VIEW

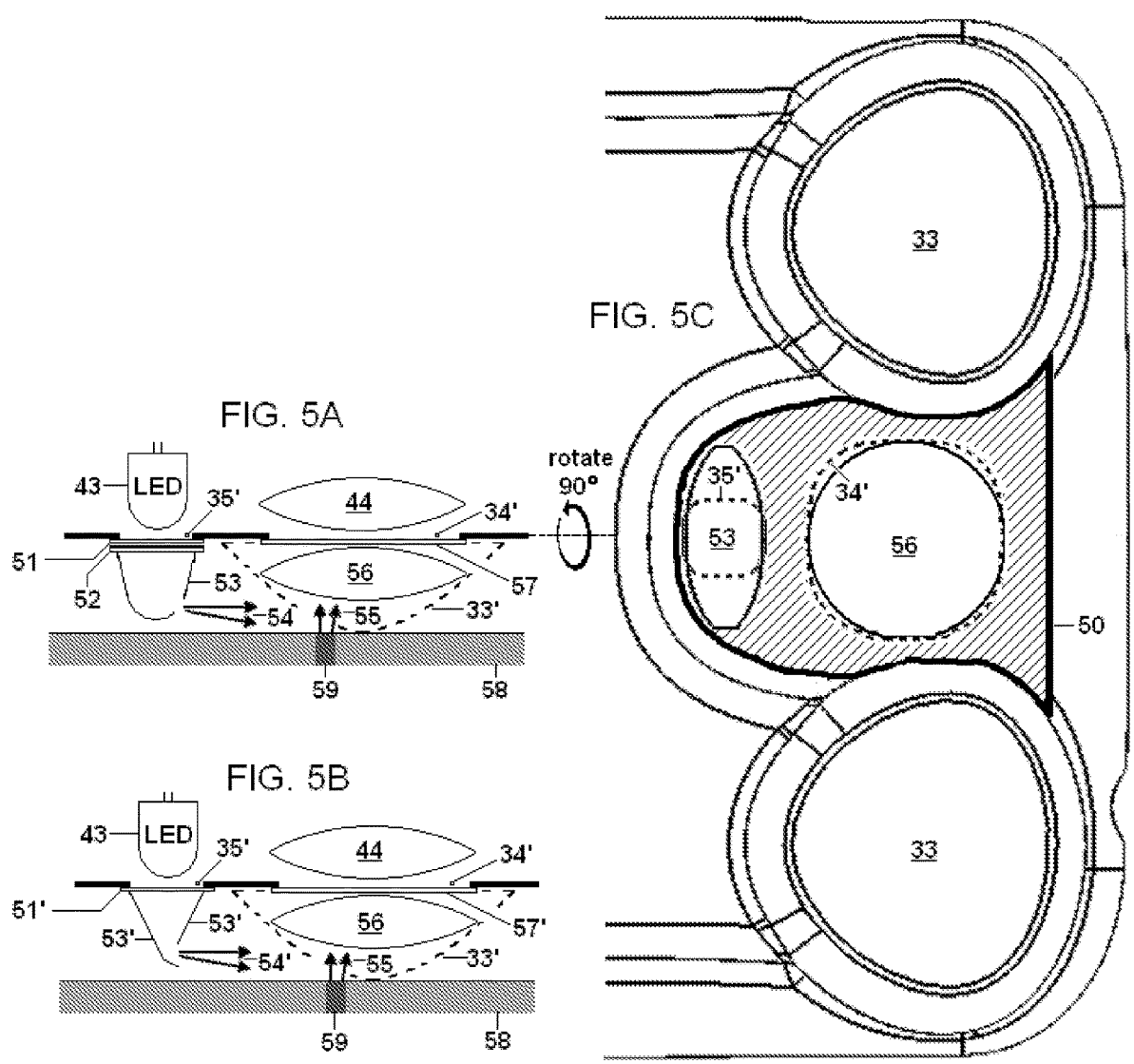

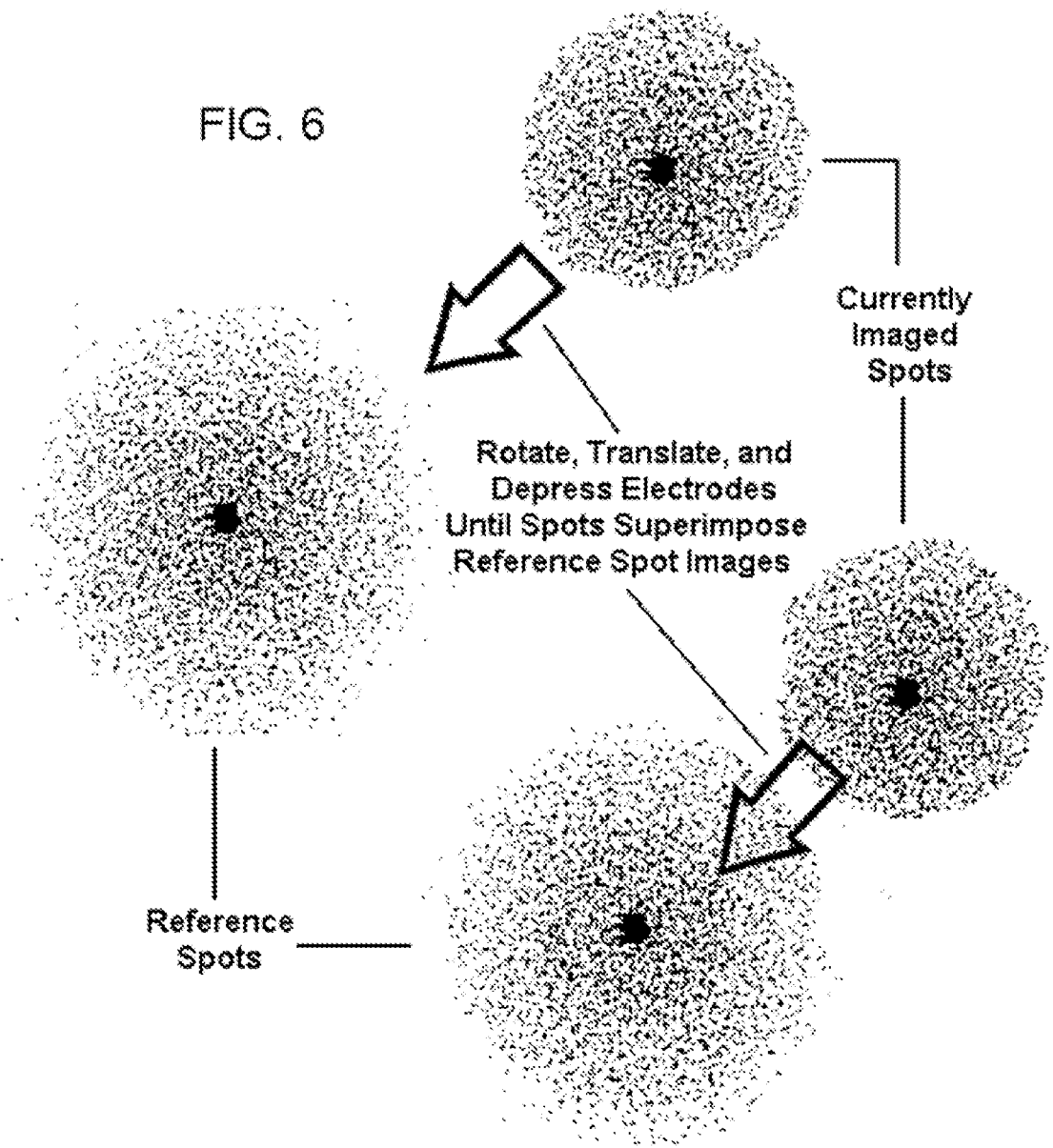

MOBILE PHONE FOR TREATING A PATIENT WITH SEIZURES

CROSS REFERENCE TO RELATED APPLICATIONS

The present application is a Continuation in Part of U.S. Nonprovisional application Ser. No. 14/292,491 filed 30 May 2014, now U.S. Pat. No. 9,375,571 issued 28 Jun. 2016, which claims the benefit of U.S. Provisional Application Ser. No. 62/001,004 filed 20 May 2014; and is a Continuation in Part of U.S. Nonprovisional application Ser. No. 13/858,114 filed 8 Apr. 2013, now U.S. Pat. No. 9,248,286 issued 2 Feb. 2016, which claims the benefit of U.S. Provisional Application Ser. No. 61/752,895 filed 15 Jan. 2013; each of which is incorporated herein by reference in its entirety for all purposes.

BACKGROUND OF THE INVENTION

The field of the present invention relates to the delivery of energy impulses (and/or fields) to bodily tissues for therapeutic purposes. The invention relates more specifically to devices and methods for treating medical conditions such as epilepsy wherein the patient uses the devices and methods as self-treatment, without the direct assistance of a healthcare professional. The energy impulses (and/or fields) that are used to treat those conditions comprise electrical and/or electromagnetic energy, delivered non-invasively to the patient, particularly to a vagus nerve of the patient.

The use of electrical stimulation for treatment of medical conditions is well known. One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference). Because the leads are implanted within the patient, the pacemaker is an example of an implantable medical device.

Another such example is electrical stimulation of the brain with implanted electrodes (deep brain stimulation), which has been approved for use in the treatment of various conditions, including pain and movement disorders such as essential tremor and Parkinson's disease [Joel S. PERLMUTTER and Jonathan W. Mink. Deep brain stimulation. Annu. Rev. Neurosci 29 (2006):229-257].

Another application of electrical stimulation of nerves is the treatment of radiating pain in the lower extremities by stimulating the sacral nerve roots at the bottom of the spinal cord [Paul F. WHITE, Shitong Li and Jen W. Chiu. Electroanalgesia: Its Role in Acute and Chronic Pain Management. Anesth Analg 92(2001):505-513; patent U.S. Pat. No. 6,871,099, entitled Fully implantable microstimulator for spinal cord stimulation as a therapy for chronic pain, to WHITEHURST, et al].

The form of electrical stimulation that is most relevant to the present invention is vagus nerve stimulation (VNS, also known as vagal nerve stimulation). It was developed initially for the treatment of partial onset epilepsy and was subsequently developed for the treatment of depression and other disorders. The left vagus nerve is ordinarily stimulated at a location within the neck by first surgically implanting an electrode there and then connecting the electrode to an electrical stimulator [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al; U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009):1042-1060; GROVES DA, Brown V J. Vagal nerve stimulation: a review of its applications and potential mechanisms that mediate its clinical effects. Neurosci Biobehav Rev 29(2005):493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3, 2008):E9, pp. 1-4; ANDREWS, R. J. Neuromodulation. I. Techniques-deep brain stimulation, vagus nerve stimulation, and transcranial magnetic stimulation. Ann. N. Y. Acad. Sci. 993(2003):1-13; LABINER, D. M., Ahern, G. L. Vagus nerve stimulation therapy in depression and epilepsy: therapeutic parameter settings. Acta. Neurol. Scand. 115(2007):23-33].

Many such therapeutic applications of electrical stimulation involve the surgical implantation of electrodes within a patient. In contrast, devices used for the procedures that are disclosed here do not involve surgery, i.e., they are not implantable medical devices. Instead, the present devices and methods stimulate nerves by transmitting energy to nerves and tissue non-invasively. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that the invasive procedures insert a substance or device into or through the skin (or other surface of the body, such as a wound bed) or into an internal body cavity beyond a body orifice.

For example, transcutaneous electrical stimulation of a nerve is non-invasive because it involves attaching electrodes to the skin, or otherwise stimulating at or beyond the surface of the skin or using a form-fitting conductive garment, without breaking the skin [Thierry KELLER and Andreas Kuhn. Electrodes for transcutaneous (surface) electrical stimulation. Journal of Automatic Control, University of Belgrade 18(2, 2008):35-45; Mark R. PRAUSNITZ. The effects of electric current applied to skin: A review for transdermal drug delivery. Advanced Drug Delivery Reviews 18 (1996) 395-425]. In contrast, percutaneous electrical stimulation of a nerve is minimally invasive because it involves the introduction of an electrode under the skin, via needle-puncture of the skin.

Another form of non-invasive electrical stimulation is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body. An electric field is induced at a distance, causing electric current to flow within electrically conducting bodily tissue. The electrical circuits for magnetic stimulators are generally complex and expensive and use a high current impulse generator that may produce discharge currents of 5,000 amps or more, which is passed through the stimulator coil to produce a magnetic pulse. The principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 OHR, United Kingdom, 2006. In contrast, the magnetic stimulators that have been disclosed by the present Applicant are relatively simpler devices that use considerably smaller currents within the stimulator coils. Accordingly, they are intended to satisfy the need for simple-to-use and less expensive non-invasive magnetic stimulation devices.

Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are generally painless and may be performed without the dangers and costs of surgery. They are ordinarily performed even without the need for local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace. Furthermore, the cost of non-invasive procedures may be significantly reduced relative to comparable invasive procedures.

In co-pending, commonly assigned patent applications, Applicant disclosed noninvasive electrical vagus nerve stimulation devices, which are adapted, and for certain applications improved, in the present disclosure [application Ser. No. 13/183,765 and Publication US2011/0276112, entitled Devices and methods for non-invasive capacitive electrical stimulation and their use for vagus nerve stimulation on the neck of a patient, to SIMON et al.; application Ser. No. 12/964,050 and Publication US2011/0125203, entitled Magnetic Stimulation Devices and Methods of Therapy, to SIMON et al.; and other co-pending commonly assigned applications that are cited therein, which are herein incorporated by reference]. The present disclosure elaborates on the electrical stimulation device, rather than the magnetic stimulation device that has similar functionality, with the understanding that unless it is otherwise indicated, the elaboration could apply to either the electrical or the magnetic nerve stimulation device. Because the earlier devices have already been disclosed, the present disclosure focuses on what is new with respect to the earlier disclosures.

In the present disclosure, the stimulator is ordinarily applied by the patient himself or herself, without the benefit of having a trained healthcare provider nearby. The primary advantage of the self-stimulation therapy is that it can be administered more or less immediately when symptoms occur, rather than having to visit the healthcare provider at a clinic or emergency room. In addition, the patient may administer the therapy on a daily basis (e.g., one or multiple times/day) to prophylactically treat the disorder. The need for such a visit would only compound the aggravation that the patient is already experiencing. Another advantage of the self-stimulation therapy is the convenience of providing the therapy in the patient's home or workplace, which eliminates scheduling difficulties, for example, when the nerve stimulation is being administered for prophylactic reasons at odd hours of the day. Furthermore, the cost of the treatment may be reduced by not requiring the involvement of a trained healthcare provider.

For the present medical applications, an electrical stimulator device is ordinarily applied to the patient's neck. In a preferred embodiment of the invention, the stimulator comprises two electrodes that lie side-by-side within separate stimulator assemblies, wherein the electrodes are separated by electrically insulating material. Each electrode and the patient's skin are in connected electrically through an electrically conducting medium that extends from the skin to the electrode.

The position and angular orientation of the device are adjusted about a location on the neck until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. The stimulator signal waveform may have a frequency and other parameters that are selected to produce a therapeutic result in the patient.

The electrical stimulation is then typically applied for 90 seconds to 30 minutes (usually 90-180 seconds), which is often sufficient to at least partially relieve headache pain within 5 minutes. The treatment then causes patients to experience a very rapid relief from headache pain, as well as a rapid opening of the nasal passages within approximately 20 minutes. Effects of the treatment may last for 4 to 5 hours or longer.

Despite the advantages of having a patient administer the nerve stimulation by him or herself, such self-stimulation presents certain risks and difficulties relating to safety and efficacy. In some situations, the vagus nerve stimulator should be applied to the left or to the right vagus nerve, but not vice versa. For example, if the stimulator is applied to the left vagus nerve at the neck, it would work as prescribed, but if it were to be accidentally applied to the right vagus nerve, the device could potentially cause cardiac problems. On the other hand, in some situations the stimulation may actually be most beneficial if applied to the right vagus nerve, and it may be relatively less effective if applied to the left vagus nerve. Therefore, if the patient is using the vagus nerve stimulator by himself or herself, it would be useful for the device be designed so that it can be used only on the prescribed side of the neck. The present invention discloses methods for preventing inadvertent stimulation on the side of the neck that is not prescribed.

Another issue concerns the positioning of the vagus nerve stimulator on the neck of the patient. Although the stimulator is designed to be robust against very small variations in position of the stimulator relative to the vagus nerve, there is nevertheless an optimal position that would preferably be maintained throughout the stimulation session in order to achieve maximum effectiveness from the stimulation. The patient will sense whether the nerve is being stimulated and can adjust the position of the stimulator in search for the optimum, but the patient also has the option of adjusting the amplitude of the stimulation in an attempt to compensate for a sub-optimal position. However, the ability to compensate using stimulation-amplitude control is limited by the likelihood that the skin and other tissue in the vicinity of the nerve may become uncomfortable if the amplitude of stimulation becomes too high. A related problem is that fluctuating movement of the stimulator relative to nerve being stimulated is to some extent unavoidable, due for example to neck muscle contractions that accompany breathing. The combination of sub-optimal positioning of the device on the neck and unavoidable movement of the device makes it difficult to assure that the patient is receiving exactly the prescribed stimulation dose in each stimulation session.

Another problem is that the patient may wish to stop the stimulation session based only on some subjective assessment of whether the stimulation has sufficiently relieved the symptoms. However, there may be a diminishing effectiveness if the stimulation session is too long, for the following reason. Let the numerical value of the accumulated effects of vagus nerve stimulation be denoted as S(t). It may for present exemplary purposes be represented as a function that increases at a rate proportional to the stimulation voltage V in the vicinity of the nerve and decays with a time constant $\tau_P$, such that after prolonged stimulation, the accumulated stimulation effectiveness may saturate at a value equal to the product of V and $\tau_P$. Thus, if $T_P$ is the duration of a vagus nerve stimulation in a particular treatment session, then for time $t<T_P$, $S(t)=V\tau_P [1-\exp(-t/\tau_P)]+S_0 \exp(-t/\tau_P)$, and for $t>T_P$, $S(t)=S(T_P) \exp(-[t-T_P]/\tau_P)$, where the time t is measured from the start of a stimulus, and $S_0$ is the value of S when $t=0$. The optimal duration of a stimulation session may be different from patient to patient, because the decay time constant $\tau_P$ may vary from patient to patient. To the extent that the stimulation protocol is designed to treat each patient individually, such that subsequent treatment sessions are designed in view of the effectiveness of previous treatment sessions, it is would be useful for the stimulation amplitude V be as constant as possible, and the treatment session should take into account the above-mentioned principle of diminishing returns. At a minimum, the average stimulation amplitude in a session should be estimated or evaluated, despite movement of the stimulator relative to the nerve and despite amplitude adjustment by the patient.

These potential problems, related to placement and movement of the stimulator, do not arise in patients in whom a stimulator electrode has been implanted about a vagus nerve. They are also of minor significance in situations where a healthcare provider is responsible for careful usage of noninvasive stimulator devices, rather than the patient. More generally, when the patient performs self-stimulation with the nerve stimulator, practical matters arise such as: how to maintain and charge the stimulator device, how to enable the patient to initiate a stimulation session, how to design the stimulation session based on the present medical circumstances of the patient, how to monitor operation of the device taking into account all of the factors that may influence a successful treatment session, and how to evaluate the success of the treatment session when it is finished. Furthermore, when the patient is able to perform self-stimulation, administrative matters such as maintaining medical records and billing should be addressed. The present invention is intended to address many such problems. The invention comprises several components, each of which may be involved in the solution of different problems, such that the system as a whole is more functional than the component parts considered individually.

SUMMARY OF THE INVENTION

The present invention involves devices and methods for the self-treatment of a epilepsy by a patient through electrical stimulation of one or more nerves within the patient. Devices are disclosed that allow the stimulation to be performed noninvasively, wherein electrodes are placed against the skin of the patient. In preferred embodiments of the invention, the selected nerve is a vagus nerve that lies under the skin of the patient's neck.

In one aspect of the invention, a nerve stimulation system comprises a mobile phone that can be used for dual purposes: (1) as a phone, such as a smartphone that would contain all of the typical features of such a phone (e.g., voice communication, Wi-Fi, web browsing, texting, email connectivity, etc.); and (2) as a nerve stimulation device incorporated into, or joined to and electrically connected with, the mobile phone. The nerve stimulation device preferably comprises one or more electrodes extending from an outer surface of the phone housing. The electrodes are configured to apply one or more electrical impulses through the surface of a patient's skin to a nerve within the patient, such as the vagus nerve. A signal generator is coupled to the electrodes for applying the electrical impulses to the electrodes, and a power source is coupled to the signal generator and/or the electrodes for providing power.

In one embodiment, the waveform of the signal that is to be applied to the patient is first created in a device exterior to, and remote from, the mobile phone housing. The mobile phone preferably includes a software application that can be downloaded into the phone to receive the waveform from the exterior device and then provide the electrical waveform signal to the electrodes. In certain embodiments, the system further includes an amplifier coupled to the electrodes to amplify the signal generated by the application software and then apply the amplified signal to the electrodes. The amplifier may be incorporated into the phone, or joined to and connected to the phone, or it may be a separate device that can be plugged into the phone to couple the amplifier with the software application and the electrodes. In one embodiment, the amplifier includes a connector that connects to the speaker output or the earphone jack socket in the mobile phone, amplifying a pseudo-audio stereo waveform signal that is produced by the smartphone, and driving the electrodes with that signal.

The system is designed to address particular problems that arise during self-treatment, when a medical professional is not present. Such problems include assuring that the patient stimulates a vagus nerve on a prescribed side of the neck (left or right), minimizing or documenting motion of the stimulator, documenting the patient's adjustment of the stimulation amplitude, and controlling the amount of energy that can be delivered to the patient during a stimulation session.

In one embodiment of the invention, the smartphone's rear camera is used to image fluorescent spots that had been applied to reference positions on the patient's skin above the vagus nerve. During repeated sessions of the vagus nerve stimulation, the position and orientation of the stimulator are adjusted in such a way that fluorescent spots that are imaged by the camera appear in the same way during the successive sessions. Movement of the imaged fluorescent spots may also be used to assess the extent to which the stimulator is fluctuating in position during the course of a stimulation session.

The parameters for the protocol of each stimulation session may be transmitted from an external device to the stimulator device from a physician-controlled computer, which provides authorization for the recharging of the stimulator device's batteries by a base station (typically a laptop computer). Parameters of the stimulation protocol may be varied in response to heterogeneity in the symptoms of patients. Different stimulation parameters may also be selected as the course of the patient's medical condition changes. In preferred embodiments, the disclosed stimulation methods and devices do not produce clinically significant side effects, such as agitation or anxiety, or changes in heart rate or blood pressure.

In a preferred embodiment of the invention, the stimulator housing comprises a rechargeable source of electrical power and two or more electrodes that are configured to stimulate a deep nerve. The stimulator may comprise two electrodes that lie on both sides of the hand-held stimulator housing. Each electrode may be in continuous contact with an electrically conducting medium that extends from the patient-interface stimulation element of the stimulator to the electrode. The interface element contacts the patient's skin when the device is in operation.

Current passing through an electrode may be from about 0 to about 40 mA, with voltage across the electrodes being from about 0 to about 30 volts. The current is passed through the electrodes in bursts of pulses. There may be pulses from about 1 to about 20 pulses per burst, preferably about five pulses. Each pulse within a burst has a duration from about 20 to about 1000 microseconds, preferably from about 200 microseconds. A burst followed by a silent inter-burst interval repeats from about 1 to about 5000 bursts per second (bps, similar to Hz), preferably from about 15 to about 50 bps, and even more preferably at about 25 bps. The preferred shape of each pulse is a full sinusoidal wave.

A source of power supplies a pulse of electric charge to the electrodes, such that the electrodes produce an electric current and/or an electric field within the patient. The electrical stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at about 1000 Hz. For example, the device may produce an electric field within the patient from about 10 to about 600 V/m (preferably less than about 100 V/m) and an electrical field gradient of greater than about 2 V/m/mm. Electric fields that are produced at the vagus nerve are generally sufficient to excite all myelinated A and B fibers, but not necessarily the unmyelinated C fibers. However, by using a reduced amplitude of stimulation, excitation of A-delta and B fibers may also be avoided.

The preferred stimulator shapes an elongated electric field of effect that can be oriented parallel to a long nerve, such as a vagus. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves in the skin that produce pain.

A method for treating a patient with seizures, such as epileptic seizures, according to the invention comprises generating an electrical signal sufficient to modulate a vagus nerve within the patient, wirelessly transmitting the electric signal to a handheld stimulator, contacting an outer surface of a skin of the patient with a contact surface of the handheld stimulator and applying one or more electrical impulses to the outer surface of the patient's skin such that the electrical impulses pass through the patient's skin transcutaneously to the vagus nerve. The electric impulses are sufficient to modulate the nerve and ameliorate the seizures.

In one embodiment, the method comprises a therapy regimen wherein the patient applies the electrical stimulation therapy multiple times/day to prophylactically treat the seizure condition. Each treatment preferably lasts from about 60 seconds and to about 5 minutes. Applicant has discovered that stimulation of the vagus nerve over a short period of time multiple times per day can significantly alleviate a patient's seizures over a period of time. In this manner, a continuous stimulation of the vagus nerve is not required to produce significant clinical results, such as those found with implantable vagal nerve stimulators that continuously stimulate the vagus nerve about 24 hours/day. This discovery allows a patient to self-treat the epilepsy condition with a handheld non-invasive electrical stimulation device at home.

In another embodiment, a method of the present invention comprises forecasting a seizure and acutely administering the stimulation therapy prior to the onset of the seizure to avert the seizure from occurring. Forecasting and averting of an acute event is implemented within the context of control theory. A controller, comprising the disclosed vagus nerve stimulator, a PID, and a feedforward model, provides input to the physiological system that is to be controlled. Output from the system is monitored in a patient using sensors for physiological signals. Those signals may then be used to provide feedback to the controller.

In closed-loop mode, the controller and system are used to select parameters for the vagus nerve stimulation. Closed loop mode may also be used when the physiological system is non-stationary. Otherwise, the controller may be used to forecast the imminence of an acute event, and the vagus nerve stimulator is used in open loop mode to stimulate the patient, but using stimulator parameters that had been selected when the system was used in closed-loop mode.

Forecasting models may be grey-box models that incorporate knowledge of the physiological system's anatomy and mechanisms. Forecasting models may also be black box models, comprising autoregressive models as well as models that make use of principal components, Kalman filters, wavelet transforms, hidden Markov models, artifical neural networks, and/or support vector machines. In the preferred embodiments, support vector machines are used.

The novel systems, devices and methods for treating epilepsy are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference. If any disclosures are incorporated herein by reference and such disclosures conflict in part and/or in whole with the present disclosure, then to the extent of conflict, and/or broader disclosure, and/or broader definition of terms, the present disclosure controls. If such disclosures conflict in part and/or in whole with one another, then to the extent of conflict, the later-dated disclosure controls.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 1B shows functional networks within the brain (resting state networks) that may be modulated by electrical stimulation of a vagus nerve.

FIG. 3A is a front view of a dual-electrode stimulator according to an embodiment of the present invention, showing that the stimulator device comprises a smartphone; FIG. 3B is a back view of the dual-electrode stimulator shown in FIG. 3A; and FIG. 3C is a side view of the dual-electrode stimulator shown in FIG. 3A.

FIG. 5A illustrates a cross-sectional view of an optical assembly used to shift illumination of a smartphone flash LED from visible to infrared light and to use that infrared light to excite and image fluorescence from material placed in the patient's skin; FIG. 5B illustrates a cross-sectional view of an optical assembly used to excite and image fluorescence from material placed in the patient's skin, when the shifting of the wavelength of LED light is not needed; and FIG. 5C rotates the view shown in FIG. 5A by 90 degrees, showing where the optical assembly is snapped into the stimulator between the electrode surfaces.

FIG. 6 shows how a continuously imaged fluorescence image of two spots is superimposed onto a reference image of those spots, in order to optimally position the stimulator.

DETAILED DESCRIPTION OF THE PREFERRED EMBODIMENTS

Figure 1A:
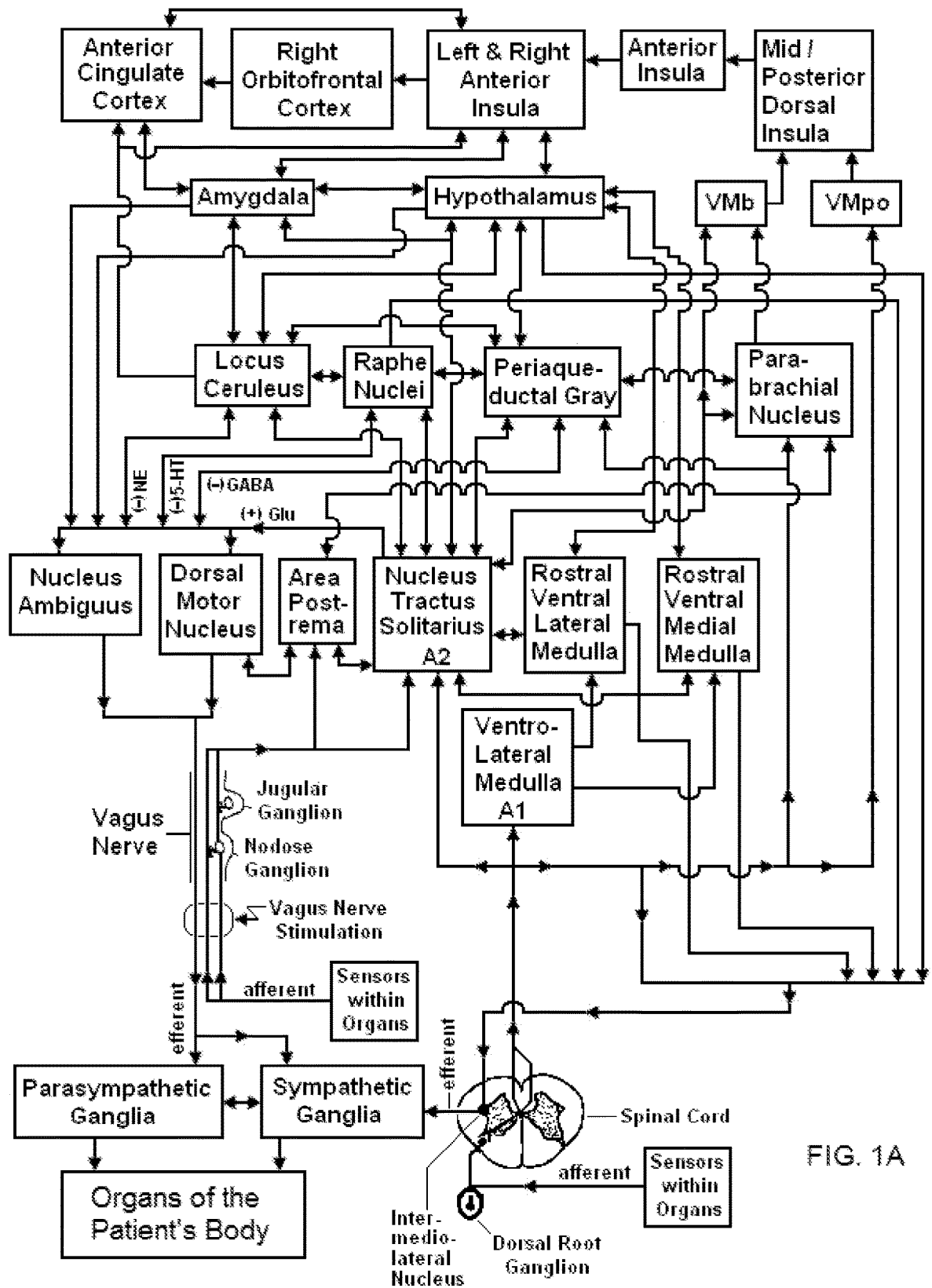
FIG. 1A shows structures within a patient's nervous system that may be modulated by electrical stimulation of a vagus nerve.

In the present invention, electrodes applied to the skin of the patient generate currents within the tissue of the patient. An objective of one embodiment of the invention is to produce and apply the electrical impulses so as to interact with the signals of one or more nerves, in order to achieve the therapeutic result. Much of the disclosure will be directed specifically to treatment of a patient by stimulation in or around a vagus nerve, with devices positioned non-invasively on or near a patient's neck to treat seizures, such as epileptic seizures. There is a large literature on methods for forecasting epilepsy seizures. Current methods have been the subject of several reviews [Brian LITT and Javier Echauz. Prediction of epileptic seizures. Lancet Neurology 1(2002): 22-30; MORMANN F, Andrzejak R G, Elger C E, Lehnertz K. Seizure prediction: the long and winding road. Brain 130(Pt 2, 2007):314-33; MORMANN F, Kreuz T, Rieke C, Andrzejak R G, Kraskov A, David P, Elger C E, Lehnertz K. On the predictability of epileptic seizures. Clin Neurophysiol 116(3, 2005):569-87; MORMANN F, Elger C E, Lehnertz K. Seizure anticipation: from algorithms to clinical practice. Curr Opin Neurol 19(2, 2006):187-93]. Tools are also available for the development of new methods for forecasting epilepsy seizures [TEIXEIRA CA, Direito B, Feldwisch-Drentrup H, Valderrama M, Costa R P, Alvarado-Rojas C, Nikolopoulos S, Le Van Quyen M, Timmer J, Schelter B, Dourado A. EPILAB: a software package for studies on the prediction of epileptic seizures. J Neurosci Methods. 200(2, 2011): 257-71].

The brain-wave data used to make the forecast are either from electrodes that are implanted in the patient's brain, or from electroencephalographic electrodes that are worn or attached to the patient's scalp [CASSON A, Yates D, Smith S, Duncan J, Rodriguez-Villegas E. Wearable electroencephalography. What is it, why is it needed, and what does it entail? IEEE Eng Med Biol Mag. 29(3, 2010):44-56]. Additional data may also be useful in making the forecast, such as data concerning heart rate [DELAMONT R S, Julu P O, Jamal G A. Changes in a measure of cardiac vagal activity before and after epileptic seizures. Epilepsy Res 35(2, 1999):87-94]. Thus, VALDERRAMA et al. are able to improve the forecast of a seizure by including the analysis of ECG data with EEG data [M. VALDERRAMA, S. Nikolopoulos, C. Adam, Vincent Navarro and M. Le Van Quyen. Patient-specific seizure prediction using a multi-feature and multi-modal EEG-ECG classification. XII Mediterranean Conference on Medical and Biological Engineering and Computing 2010, IFMBE Proceedings, 2010, Volume 29, Part 1, 77-80]. Lack of sleep and the patient's self-prediction of whether a seizure is imminent may also useful in making a forecast [HAUT SR, Hall C B, Masur J, Lipton R B. Seizure occurrence: precipitants and prediction. Neurology. 69(20, 2007):1905-10]. Motion data collected using an accelerometer may be useful for detecting artifacts [Sweeney K T, Leamy D J, Ward T E, McLoone S. Intelligent artifact classification for ambulatory physiological signals. Conf Proc IEEE Eng Med Biol Soc. 2010; 2010:6349-52].

Proposed countermeasures against the forecasted epileptic seizures comprise: on-demand excretion of fast-acting anticonvulsant substances, local cooling, biofeedback operant conditioning, and electrical or other stimulation to reset brain dynamics to a state that will not develop into a seizure [STACEY WC, Litt B. Technology insight: neuroengineering and epilepsy-designing devices for seizure control. Nat Clin Pract Neurol 4(4, 2008):190-201]. The electrical stimulation countermeasures that have been proposed involved deep-brain stimulation or other uses of implanted electrodes, including implanted vagus nerve stimulators, but not non-invasive vagal nerve stimulation. Non-invasive magnetic stimulation has also been proposed, but not of the vagus nerve. [THEODORE WH, Fisher R. Brain stimulation for epilepsy. Acta Neurochir Suppl. 97(2, 2007):261-72]. Most electrical stimulation countermeasures involve open-loop devices, meaning that there is no direct feedback to the electrical stimulator from sensors that can be used to forecast or monitor the epileptic seizure. More recently, closed-loop stimulators have also been described wherein there may be feedback to the electrical stimulator from the sensors. Closed-loop therapy has the potential advantage that it may be precisely timed or dosed to be administered only when and where needed, for example, administered immediately upon or before seizure detection, directly to the site of seizure origin and with variable dose depending upon detected seizure characteristics [U.S. Pat. No. 6,480,743, entitled System and method for adaptive brain stimulation, to Kirkpatrick et al; U.S. Pat. No. 7,231,254, entitled Closed-loop feedback-driven neuromodulation, to DiLorenzo; U.S. Pat. No. 7,209,787, entitled Apparatus and method for closed-loop intracranial stimulation for optimal control of neurological disease, to DiLorenzo].

It should be noted that some patients are able to predict their own epileptic seizures well in advance, and some are able to do so reliably [HAUT SR, Hall C B, LeValley A J, Lipton R B. Can patients with epilepsy predict their seizures? Neurology. 68(4, 2007):262-6; STACEY WC, Litt B. Technology insight: neuroengineering and epilepsy-designing devices for seizure control. Nat Clin Pract Neurol 4(4, 2008):190-201]. Accordingly, one aspect of the present invention comprises the steps of (1) a patient predicts his/her own epileptic seizure, or a device predicts the seizure using data obtained from EEG devices plus accessory noninvasive data (e.g., heart rate, and motion), as described in publications such as the ones cited above; and (2) the patient or a caregiver performs noninvasive vagal nerve stimulation using devices that are disclosed herein. The rationale for performing the vagal nerve stimulation is that it is already an adjunctive therapy for pharmaco-resistant partial epilepsy, having been approved since 1997 by the FDA. This includes the use of vagal nerve stimulation performed on-demand by the epileptic patient [BOON, P., Vonck, K., Van Walleghem, P., D'Have, M., Goossens, L., Vandekerckhove, T., Caemaert, J., De Reuck, J., Programmed and magnet-induced vagus nerve stimulation for refractory epilepsy. J. Clin. Neurophysiol. 18(2001):402-407; MORRIS III, G. L., 2003. A retrospective analysis of the effects of magnet-activated stimulation in conjunction with vagus nerve stimulation therapy. Epilepsy Behav. 4(2003): 740-745]. A novelty of the present disclosure is that the vagus nerve stimulation is performed noninvasively and in anticipation of an imminent attack.

In another application of the invention, the non-invasive vagus nerve stimulators disclosed herein can be used chronically and prophylactically by a caregiver or the patient to limit or prevent seizures. Implantable vagus nerve stimulators, such as those described above, have been used for years to minimize or eliminate epileptic seizures. However, these devices should be implanted into the patient's neck, which is a costly, invasive and permanent procedure. With the present invention, the patient can stimulate his/her vagus nerve non-invasively on a regular basis every day to obtain the same results as those obtained by the implantable VNS devices. In this aspect of the invention, the patient would work with her/her physician to determine the appropriate number and intervals for non-invasive stimulation to effectively limit or prevent seizures. In addition, if the patient experiences prodromal symptoms that a seizure is about to occur, he/she can use the non-invasive device immediately to acutely limit or prevent the seizure from occurring.

However, it should be appreciated that the nerve stimulation may also result in other benefits to the patient such as: relaxation of the smooth muscle of the bronchia for treatment of bronchoconstriction associated with asthma, COPD and/or exercised-induced bronchoconstriction, increase in blood pressure associated with orthostatic hypotension, reduction in blood pressure that may be associated with, for example, refractory hypertension, treating ileus conditions, neuropsychiatric disorders, such as depression, anxiety and/or personality disorders, anaphylaxis, obesity and/or type II diabetes, a neurodegenerative disorder such as dementia and/or Alzheimer's disease, migraine, tension-type, cluster, MOH and other types of headache, rhinitis, sinusitis, stroke, atrial fibrillation, autism, modulation of liver function, gastroparesis and other functional gastrointestinal disorders, movement disorders, CHF, chronic pain, fibromyalgia, metabolic or thyroid disorders, cardiovascular disease, and/or any other ailment that may be affected by nerve transmissions of a vagus nerve. Such treatments for different disorders are disclosed in the following US patent applications assigned to ElectroCore, LLC (the complete disclosures of which are incorporated by reference in their entirety for all purposes): U.S. patent application Ser. No. 13/858,114, filed Apr. 8, 2013 (ELEC-47), U.S. patent application Ser. No. 13/783,391, filed Mar. 3, 2013 (ELEC-49), U.S. patent application Ser. No. 13/736,096, filed Jan. 8, 2013 (ELEC-43), U.S. patent application Ser. No. 13/731,035, filed Dec. 30, 2012 (ELEC-46), U.S. patent application Ser. No. 13/603,799 filed Sep. 5, 2012 (ELEC-44-1), U.S. patent application Ser. No. 13/357,010, filed Jan. 24, 2012 (ELEC-41), U.S. patent application Ser. No. 13/279,437 filed Oct. 24, 2011 (ELEC-40), U.S. patent application Ser. No. 13/222,087 filed Aug. 31, 2011 (ELEC-39), U.S. patent application Ser. No. 13/183,765 filed Jul. 15, 2011 (ELEC-38), U.S. patent application Ser. No. 13/183,721 filed Jul. 15, 2011, now U.S. Pat. No. 8,676,330 issued Mar. 18, 2014 (ELEC-36), U.S. patent application Ser. No. 13/109,250 filed May 17, 2011, now U.S. Pat. No. 8,676,324 issued Mar. 18, 2014 (ELEC-37), U.S. patent application Ser. No. 13/075,746 filed Mar. 30, 2011 (ELEC-35), U.S. patent application Ser. No. 13/024,727, filed Feb. 10, 2011 (ELEC-34), U.S. patent application Ser. No. 13/005,005 filed Jan.

12, 2011 (ELEC-33), U.S. patent application Ser. No. 12/964,050 filed Dec. 9, 2010 (ELEC-32), U.S. patent application Ser. No. 12/859,568 filed Aug. 9, 2010 (ELEC-31), U.S. patent application Ser. No. 12/408,131 filed Mar. 20, 2009 (ELEC-17CP1) and U.S. patent application Ser. No. 12/612,177 filed Nov. 9, 2009 now U.S. Pat. No. 8,041,428 issued Oct. 18, 2011 (ELEC-14CP1).

It will also be appreciated that the devices and methods of the present invention can be applied to other tissues and nerves of the body, including but not limited to other parasympathetic nerves, sympathetic nerves, spinal or cranial nerves. In one embodiment, the devices of the present invention are applied to the trigeminal nerve to treat a variety of medical disorders, including but not limited to headache, such as migraine, tension type headache, chronic headache and/or occipital neuralgia. In this embodiment, the devices described below are placed against the patient's forehead and electrical impulses are applied transcutaneously through the patient's skin to the supratrochear and/or supraorbital branches of the trigeminal nerve sufficient to stimulate the nerve and relieve pain associated with headache. Such treatments of these conditions are described more fully in the following patents/patent applications (the complete disclosures of which are hereby incorporated by reference in their entirety for all purposes): US Patent Publication Numbers 2013/0282095, 2009/0210028, 2007/0276451 and U.S. Pat. No. 8,428,734.

The fact that electrical stimulation of a vagus nerve can be used to treat so many disorders may be understood as follows. The vagus nerve is composed of motor and sensory fibers. The vagus nerve leaves the cranium, passes down the neck within the carotid sheath to the root of the neck, then passes to the chest and abdomen, where it contributes to the innervation of the viscera. A human vagus nerve (tenth cranial nerve, paired left and right) consists of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system.

The largest nerve fibers within a left or right vagus nerve are approximately 20 µm in diameter and are heavily myelinated, whereas only the smallest nerve fibers of less than about 1 µm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 µm diameter), A-beta fibers (afferent or efferent fibers, 5-12 µm), A-gamma fibers (efferent fibers, 3-7 µm), A-delta fibers (afferent fibers, 2-5 µm), B fibers (1-3 µm) and C fibers (unmyelinated, 0.4-1.2 µm). The diameters of group A and group B fibers include the thickness of the myelin sheaths.

The vagus (or vagal) afferent nerve fibers arise from cell bodies located in the vagal sensory ganglia, which take the form of swellings near the base of the skull. Vagal afferents traverse the brainstem in the solitary tract, with some eighty percent of the terminating synapses being located in the nucleus of the tractus solitarius (or nucleus tractus solitarii, nucleus tractus solitarius, or NTS). The NTS projects to a wide variety of structures in the central nervous system, such as the amygdala, raphe nuclei, periaqueductal gray, nucleus paragigantocellurlais, olfactory tubercule, locus ceruleus, nucleus ambiguus and the hypothalamus. The NTS also projects to the parabrachial nucleus, which in turn projects to the hypothalamus, the thalamus, the amygdala, the anterior insula, and infralimbic cortex, lateral prefrontal cortex, and other cortical regions [JEAN A. The nucleus tractus solitarius: neuroanatomic, neurochemical and functional aspects. Arch Int Physiol Biochim Biophys 99(5, 1991):A3-A52]. Thus, stimulation of vagal afferents can modulate the activity of many structures of the brain and brainstem through these projections.

With regard to vagal efferent nerve fibers, two vagal components have evolved in the brainstem to regulate peripheral parasympathetic functions. The dorsal vagal complex, consisting of the dorsal motor nucleus and its connections controls parasympathetic function primarily below the level of the diaphragm, while the ventral vagal complex, comprised of nucleus ambiguus and nucleus retrofacial, controls functions primarily above the diaphragm in organs such as the heart, thymus and lungs, as well as other glands and tissues of the neck and upper chest, and specialized muscles such as those of the esophageal complex. For example, the cell bodies for the preganglionic parasympathetic vagal neurons that innervate the heart reside in the nucleus ambiguus, which is relevant to potential cardiovascular side effects that may be produced by vagus nerve stimulation.

The vagus efferent fibers innervate parasympathetic ganglionic neurons that are located in or adjacent to each target organ. The vagal parasympathetic tone resulting from the activity of these fibers is balanced reflexively in part by sympathetic innervations. Consequently, electrical stimulation of a vagus nerve may result not only in modulation of parasympathetic activity in postganglionic nerve fibers, but also a reflex modulation of sympathetic activity. The ability of a vagus nerve to bring about widespread changes in autonomic activity, either directly through modulation of vagal efferent nerves, or indirectly via activation of brainstem and brain functions that are brought about by electrical stimulation of vagal afferent nerves, accounts for the fact that vagus nerve stimulation can treat many different medical conditions in many end organs. Selective treatment of particular conditions is possible because the parameters of the electrical stimulation (frequency, amplitude, pulse width, etc.) may selectively activate or modulate the activity of particular afferent or efferent A, B, and/or C fibers that result in a particular physiological response in each individual.

As ordinarily practiced, the electrodes used to stimulate a vagus nerve are implanted about the nerve during open neck surgery. For many patients, this may be done with the objective of implanting permanent electrodes to treat epilepsy, depression, or other conditions [Arun Paul AMAR, Michael L. Levy, Charles Y. Liu and Michael L. J. Apuzzo. Chapter 50. Vagus nerve stimulation. pp. 625-638, particularly 634-635. In: Elliot S. Krames, P. Hunber Peckham, Ali R. Rezai, eds. Neuromodulation. London: Academic Press, 2009; KIRSE DJ, Werle A H, Murphy J V, Eyen T P, Bruegger D E, Hornig G W, Torkelson R D. Vagus nerve stimulator implantation in children. Arch Otolaryngol Head Neck Surg 128(11, 2002):1263-1268]. In that case, the electrode is often a spiral electrode, although other designs may be used as well [U.S. Pat. No. 4,979,511, entitled Strain relief tether for implantable electrode, to TERRY, Jr.; U.S. Pat. No. 5,095,905, entitled Implantable neural electrode, to KLEPINSKI]. In other patients, a vagus nerve is electrically stimulated during open-neck thyroid surgery in order to confirm that the nerve has not been accidentally damaged during the surgery. In that case, a vagus nerve in the neck is surgically exposed, and a temporary stimulation electrode is clipped about the nerve [SCHNEIDER R, Randolph G W, Sekulla C, Phelan E, Thanh P N, Bucher M, Machens A, Dralle H, Lorenz K. Continuous intraoperative vagus nerve stimulation for identification of imminent recurrent laryngeal nerve injury. Head Neck. 2012 Nov. 20. doi: 10.1002/hed.23187 (Epub ahead of print, pp. 1-8)].

It is also possible to electrically stimulate a vagus nerve using a minimally invasive surgical approach, namely percutaneous nerve stimulation. In that procedure, a pair of electrodes (an active and a return electrode) are introduced through the skin of a patient's neck to the vicinity of a vagus nerve, and wires connected to the electrodes extend out of the patient's skin to a pulse generator [Publication number US20100241188, entitled Percutaneous electrical treatment of tissue, to J. P. ERRICO et al.; SEPULVEDA P, Bohill G, Hoffmann T J. Treatment of asthmatic bronchoconstriction by percutaneous low voltage vagal nerve stimulation: case report. Internet J Asthma Allergy Immunol 7(2009):e1 (pp 1-6); MINER, J. R., Lewis, L. M., Mosnaim, G. S., Varon, J., Theodoro, D. Hoffman, T. J. Feasibility of percutaneous vagus nerve stimulation for the treatment of acute asthma exacerbations. Acad Emerg Med 2012; 19: 421-429], the complete disclosures of which are incorporated herein by reference in their entirety for all purposes.

Percutaneous nerve stimulation procedures had previously been described primarily for the treatment of pain, but not for a vagus nerve, which is ordinarily not considered to produce pain and which presents special challenges [HUNTOON MA, Hoelzer B C, Burgher A H, Hurdle M F, Huntoon E A. Feasibility of ultrasound-guided percutaneous placement of peripheral nerve stimulation electrodes and anchoring during simulated movement: part two, upper extremity. Reg Anesth Pain Med 33(6, 2008):558-565; CHAN I, Brown A R, Park K, Winfree C J. Ultrasound-guided, percutaneous peripheral nerve stimulation: technical note. Neurosurgery 67(3 Suppl Operative, 2010):ons136-139; MONTI E. Peripheral nerve stimulation: a percutaneous minimally invasive approach. Neuromodulation 7(3, 2004):193-196; Konstantin V SLAVIN. Peripheral nerve stimulation for neuropathic pain. US Neurology 7(2, 2011): 144-148].

In one embodiment, the stimulation device is introduced through a percutaneous penetration in the patient to a target location within, adjacent to, or in close proximity with, the carotid sheath that contains the vagus nerve. Once in position, electrical impulses are applied through the electrodes of the stimulation device to one or more selected nerves (e.g., vagus nerve or one of its branches) to stimulate, block or otherwise modulate the nerve(s) and treat the patient's condition or a symptom of that condition. For some conditions, the treatment may be acute, meaning that the electrical impulse immediately begins to interact with one or more nerves to produce a response in the patient. In some cases, the electrical impulse will produce a response in the nerve(s) to improve the patient's condition or symptom in less than 3 hours, preferably less than 1 hour and more preferably less than 15 minutes. For other conditions, intermittently scheduled or as-needed stimulation of the nerve may produce improvements in the patient over the course of several days, weeks, months or years. A more complete description of a suitable percutaneous procedure for vagal nerve stimulation can be found in commonly assigned, co-pending U.S. patent application titled "Percutaneous Electrical Treatment of Tissue", filed Apr. 13, 2009 (Ser. No. 12/422,483), the complete disclosure of which is hereby incorporated by reference in its entirety for all purposes.

In another embodiment of the invention, a time-varying magnetic field, originating and confined to the outside of a patient, generates an electromagnetic field and/or induces eddy currents within tissue of the patient. In another embodiment, electrodes applied to the skin of the patient generate currents within the tissue of the patient. An objective of the invention is to produce and apply the electrical impulses so as to interact with the signals of one or more nerves, in order to prevent or avert a stroke and/or transient ischemic attack, to ameliorate or limit the effects of an acute stroke or transient ischemic attack, and/or to rehabilitate a stroke patient.

Much of the disclosure will be directed specifically to treatment of a patient by electromagnetic stimulation in or around a vagus nerve, with devices positioned non-invasively on or near a patient's neck. However, it will also be appreciated that the devices and methods of the present invention can be applied to other tissues and nerves of the body, including but not limited to other parasympathetic nerves, sympathetic nerves, spinal or cranial nerves. As recognized by those having skill in the art, the methods should be carefully evaluated prior to use in patients known to have preexisting cardiac issues. In addition, it will be recognized that the treatment paradigms of the present invention can be used with a variety of different vagal nerve stimulators, including implantable and/or percutaneous stimulation devices, such as the ones described above.

FIG. 1A shows the location of the stimulation as "Vagus Nerve Stimulation," relative to its connections with other anatomical structures that are potentially affected by the stimulation. In different embodiments of the invention, various brain and brainstem structures are preferentially modulated by the stimulation. These structures will be described in sections of the disclosure that follow, along with the rationale for modulating their activity as a prophylaxis or treatment for stroke or transient ischemic attack. As a preliminary matter, we first describe the vagus nerve itself and its most proximal connections, which are particularly relevant to the disclosure below of the electrical waveforms that are used to perform the stimulation.

The vagus nerve (tenth cranial nerve, paired left and right) is composed of motor and sensory fibers. The vagus nerve leaves the cranium, passes down the neck within the carotid sheath to the root of the neck, then passes to the chest and abdomen, where it contributes to the innervation of the viscera.

A vagus nerve in man consists of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system. Propagation of electrical signals in efferent and afferent directions is indicated by arrows in FIG. 1A. If communication between structures is bidirectional, this is shown in FIG. 1A as a single connection with two arrows, rather than showing the efferent and afferent nerve fibers separately.

The largest nerve fibers within a left or right vagus nerve are approximately 20 μm in diameter and are heavily myelinated, whereas only the smallest nerve fibers of less than about 1 μm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 μm diameter), A-beta fibers (afferent or efferent fibers, 5-12 μm), A-gamma fibers (efferent fibers, 3-7 μm), A-delta fibers (afferent fibers, 2-5 μm), B fibers (1-3 μm) and C fibers (unmyelinated, 0.4-1.2 μm). The diameters of group A and group B fibers include the thickness of the myelin sheaths. It is understood that the anatomy of the vagus nerve is developing in newborns and infants, which accounts in part for the maturation of autonomic reflexes. Accordingly, it is also understood that the parameters of vagus nerve stimulation in the present invention are chosen in such a way as to account for this age-related maturation [PEREYRA P M, Zhang W, Schmidt M, Becker L E. Development of myelinated and unmyelinated fibers of human vagus nerve during the first year of life. J Neurol Sci 110(1-2, 1992): 107-113; SCHECHTMAN VL, Harper R M, Kluge K A. Development of heart rate variation over the first 6 months of life in normal infants. Pediatr Res 26(4, 1989):343-346].

The vagus (or vagal) afferent nerve fibers arise from cell bodies located in the vagal sensory ganglia. These ganglia take the form of swellings found in the cervical aspect of the vagus nerve just caudal to the skull. There are two such ganglia, termed the inferior and superior vagal ganglia. They are also called the nodose and jugular ganglia, respectively (See FIG. 1A). The jugular (superior) ganglion is a small ganglion on the vagus nerve just as it passes through the jugular foramen at the base of the skull. The nodose (inferior) ganglion is a ganglion on the vagus nerve located in the height of the transverse process of the first cervical vertebra.

Vagal afferents traverse the brainstem in the solitary tract, with some eighty percent of the terminating synapses being located in the nucleus of the tractus solitarius (or nucleus tractus solitarii, nucleus tractus solitarius, or NTS, see FIG. 1A). The NTS projects to a wide variety of structures in the central nervous system, such as the amygdala, raphe nuclei, periaqueductal gray, nucleus paragigantocellurlais, olfactory tubercule, locus ceruleus, nucleus ambiguus and the hypothalamus. The NTS also projects to the parabrachial nucleus, which in turn projects to the hypothalamus, the thalamus, the amygdala, the anterior insula, and infralimbic cortex, lateral prefrontal cortex, and other cortical regions [JEAN A. The nucleus tractus solitarius: neuroanatomic, neurochemical and functional aspects. Arch Int Physiol Biochim Biophys 99(5, 1991):A3-A52]. Such central projections are discussed below in connection with the interoception and resting state neural networks.

With regard to vagal efferent nerve fibers, two vagal components have evolved in the brainstem to regulate peripheral parasympathetic functions. The dorsal vagal complex, consisting of the dorsal motor nucleus and its connections (see FIG. 1A), controls parasympathetic function primarily below the level of the diaphragm (e.g. gut and its enterochromaffin cells), while the ventral vagal complex, comprised of nucleus ambiguus and nucleus retrofacial, controls functions primarily above the diaphragm in organs such as the heart, thymus and lungs, as well as other glands and tissues of the neck and upper chest, and specialized muscles such as those of the esophageal complex. For example, the cell bodies for the preganglionic parasympathetic vagal neurons that innervate the heart reside in the nucleus ambiguus, which is relevant to potential cardiovascular side effects that may be produced by vagus nerve stimulation.

Broadly speaking, applicant has determined that there are three components to the effects of nVNS on the brain. The strongest effect occurs during the two minute stimulation and results in significant changes in brain function that can be clearly seen as acute changes in autonomic function (e.g. measured using pupillometry, heart rate variability, galvanic skin response, or evoked potential) and activation and inhibition of various brain regions as shown in fMRI imaging studies. The second effect, of moderate intensity, lasts for 15 to 180 minutes after stimulation. Animal studies have shown changes in neurotransmitter levels in various parts of the brain that persist for several hours. The third effect, of mild intensity, lasts up to 8 hours and is responsible for the long lasting alleviation of symptoms seen clinically and, for example, in animal models of migraine headache.

Thus, depending on the medical indication, whether it is a chronic or acute treatment, and the natural history of the disease, different treatment protocols may be used. In particular, applicant has discovered that it is not necessary to "continuously stimulate" the vagus nerve (or to in order to provide clinically efficacious benefits to patients with certain disorders, such as epilepsy). The term "continuously stimulate" as defined herein means stimulation that follows a certain On/Off pattern continuously 24 hours/day. For example, existing implantable vagal nerve stimulators "continuously stimulate" the vagus nerve with a pattern of 30 seconds ON/5 minutes OFF (or the like) for 24 hours/day and seven days/week. Applicant has determined that this continuous stimulation is not necessary to provide the desired clinical benefit. For example, in the treatment of epileptic seizures, the treatment paradigm may comprise two minutes of stimulation prior to the onset of a seizure, followed by another two-minute stimulation 15 minutes later. For prophylactic treatment, three 2-minute stimulations three times per day appear to be optimal. Sometimes, multiple consecutive, two minute stimulations are required. Thus, the initial treatment protocol corresponds to what may be optimum for the population of patients at large for a given condition. However, the treatment may then be modified on an individualized basis, depending on the response of each particular patient.

The present invention contemplates three types of interventions involving stimulation of a vagus nerve: prophylactic, acute and compensatory (rehabilitative). Among these, the acute treatment involves the fewest administrations of vagus nerve stimulations, which begin upon the appearance of symptoms. It is intended primarily to enlist and engage the autonomic nervous system to inhibit excitatory neurotransmissions that accompany the symptoms. The prophylactic treatment resembles the acute treatment in the sense that it is administered as though acute symptoms had just occurred (even though they have not) and is repeated at regular intervals, as though the symptoms were reoccurring (even though they are not). The rehabilitative or compensatory treatments, on the other hand, seek to promote long-term adjustments in the central nervous system, compensating for deficiencies that arose as the result of the patient's disease by making new neural circuits.

A vagus nerve stimulation treatment according to the present invention is conducted for continuous period of thirty seconds to five minutes, preferably about 90 seconds to about three minutes and more preferably about two minutes (each defined as a single dose). After a dose has been completed, the therapy is stopped for a period of time (depending on the treatment as described below). For prophylactic treatments, the therapy preferably comprises multiple doses/day over a period of time that may last from one week to a number of years. In certain embodiments, the treatment will comprise multiple doses at predetermined times during the day and/or at predetermined intervals throughout the day. In exemplary embodiments, the treatment comprises one of the following: (1) 3 doses/day at predetermined intervals or times; (2) two doses, either consecutively, or separated by 5 min at predetermined intervals or times, preferably two or three times/day; (3) 3 doses, either consecutively or separated by 5 min again at predetermined intervals or times, such as 2 or 3 times/day; or (4) 1-3 doses, either consecutively or separated by 5 min, 4-6 times per day. Initiation of a treatment may begin when an imminent seizure is forecasted, or in a risk factor reduction program it may be performed throughout the day beginning after the patient arises in the morning.

In an exemplary embodiment, each treatment session comprises 1-3 doses administered to the patient either consecutively or separated by 5 minutes. The treatment sessions are administered every 15, 30, 60 or 120 minutes during the day such that the patient could receive 2 doses every hour throughout a 24-hour day.

For certain disorders, the time of day can be more important than the time interval between treatments. For example, the locus correleus has periods of time during a 24-hour day wherein it has inactive periods and active periods. Typically, the inactive periods can occur in the late afternoon or in the middle of the night when the patient is asleep. It is during the inactive periods that the levels of inhibitory neurotransmitters in the brain that are generated by the locus correleus are reduced. This may have an impact on certain disorders. For example, patients suffering from migraines or cluster headaches often receive these headaches after an inactive period of the locus correleus. For these types of disorders, the prophylactic treatment is optimal during the inactive periods such that the amounts of inhibitory neurotransmitters in the brain can remain at a higher enough level to mitigate or abort an acute attack of the disorder.

In these embodiments, the prophylactic treatment may comprise multiple doses/day timed for periods of inactivity of the locus correleus. In one embodiment, a treatment according to the present invention comprises one or more doses administered 2-3 times per day or 2-3 "treatment sessions" per day. The treatment sessions preferably occur during the late afternoon or late evening, in the middle of the night and again in the morning when the patient wakes up. In an exemplary embodiment, each treatment session comprises 1-4 doses, preferably 2-3 doses, with each dose lasting for about 90 seconds to about three minutes.

For other disorders, the intervals between treatment sessions may be the most important as applicant has determined that stimulation of the vagus nerve can have a prolonged effect on the inhibitor neurotransmitters levels in the brain, e.g., at least one hour, up to 3 hours and sometimes up to 8 hours. In one embodiment, a treatment according to the present invention comprises one or more doses (i.e., treatment sessions) administered at intervals during a 24-hour period. In a preferred embodiment, there are 1-5 such treatment sessions, preferably 2-4 treatment sessions. Each treatment session preferably comprises 1-3 doses, each lasting between about 60 seconds to about three minutes, preferably about 90 seconds to about 150 seconds, more preferably about 2 minutes.

For an acute treatment, such as treatment of seizures, the therapy according to the present invention may comprise one or more embodiments: (1) 1 dose at the onset of symptoms; (2) 1 dose at the onset of symptoms, followed by another dose at 5-15 min; or (3) 1 dose every 15 minutes to 1 hour at the onset of symptoms until the acute attack has been mitigated or aborted. In these embodiments, each dose preferably last between about 60 seconds to about three minutes, preferably about 90 seconds to about 150 seconds, more preferably about 2 minutes.

For long term treatment of an acute insult such as one that occurs with epileptic patients, the therapy may consist of: (1) 3 treatments/day; (2) 2 treatments, either consecutively or separated by 5 min, 3×/day; (3) 3 treatments, either consecutively or separated by 5 min, 2×/day; (4) 2 or 3 treatments, either consecutively or separated by 5 min, up to 10×/day; or (5) 1, 2 or 3 treatments, either consecutively or separated by 5 min, every 15, 30, 60 or 120 min.

For all of the treatments listed above, one may alternate treatment between left and right sides, or in the case of stroke or migraine that occur in particular brain hemispheres, one may treat ipsilateral or contralateral to the stroke-hemisphere or headache side, respectively. Or for a single treatment, one may treat one minute on one side followed by one minute on the opposite side. Variations of these treatment paradigms may be chosen on a patient-by-patient basis. However, it is understood that parameters of the stimulation protocol may be varied in response to heterogeneity in the symptoms of patients. Different stimulation parameters may also be selected as the course of the patient's condition changes. In preferred embodiments, the disclosed methods and devices do not produce clinically significant side effects, such as agitation or anxiety, or changes in heart rate or blood pressure.

The prophylactic treatments may be most effective when the patient is in a prodromal, high-risk bistable state. In that state, the patient is simultaneously able to remain normal or exhibit symptoms, and the selection between normal and symptomatic states depends on the amplification of fluctuations by physiological feedback networks. For example, a thrombus may exist in either a gel or fluid phase, with the feedback amplification of fluctuations driving the change of phase and/or the volume of the gel phase. Thus, a thrombus may form or not, depending on the nonlinear dynamics exhibited by the network of enzymes involved in clot formation, as influenced by blood flow and inflammation that may be modulated by vagus nerve stimulation [PANTELEEV MA, Balandina A N, Lipets E N, Ovanesov M V, Ataullakhanov F I. Task-oriented modular decomposition of biological networks: trigger mechanism in blood coagulation. Biophys J 98(9, 2010):1751-1761; Alexey M SHIBEKO, Ekaterina S Lobanova, Mikhail A Panteleev and Fazoil I Ataullakhanov. Blood flow controls coagulation onset via the positive feedback of factor VII activation by factor Xa. BMC Syst Biol 2010; 4(2010):5, pp. 1-12]. Consequently, the mechanisms of vagus nerve stimulation treatment during prophylaxis for a stroke are generally different than what occurs during an acute treatment, when the stimulation inhibits excitatory neurotransmission that follows the onset of ischemia that is already caused by the thrombus. Nevertheless, the prophylactic treatment may also inhibit excitatory neurotransmission so as to limit the excitation that would eventually occur upon formation of a thrombus, and the acute treatment may prevent the formation of another thrombus.

The circuits involved in such inhibition are illustrated in FIG. 1A. Excitatory nerves within the dorsal vagal complex generally use glutamate as their neurotransmitter. To inhibit neurotransmission within the dorsal vagal complex, the present invention makes use of the bidirectional connections that the nucleus of the solitary tract (NTS) has with structures that produce inhibitory neurotransmitters, or it makes use of connections that the NTS has with the hypothalamus, which in turn projects to structures that produce inhibitory neurotransmitters. The inhibition is produced as the result of the stimulation waveforms that are described below. Thus, acting in opposition to glutamate-mediated activation by the NTS of the area postrema and dorsal motor nucleus are: GABA, and/or serotonin, and/or norepinephrine from the periaqueductal gray, raphe nuclei, and locus coeruleus, respectively. FIG. 1A shows how those excitatory and inhibitory influences combine to modulate the output of the dorsal motor nucleus. Similar influences combine within the NTS itself, and the combined inhibitory influences on the NTS and dorsal motor nucleus produce a general inhibitory effect.

The activation of inhibitory circuits in the periaqueductal gray, raphe nuclei, and locus coeruleus by the hypothalamus or NTS may also cause circuits connecting each of these structures to modulate one another. Thus, the periaqueductal gray communicates with the raphe nuclei and with the locus coeruleus, and the locus coeruleus communicates with the raphe nuclei, as shown in FIG. 1A [PUDOVKINA OL, Cremers T I, Westerink B H. The interaction between the locus coeruleus and dorsal raphe nucleus studied with dual-probe microdialysis. Eur J Pharmacol 7(2002); 445(1-2):37-42.; REICHLING DB, Basbaum A I. Collateralization of periaqueductal gray neurons to forebrain or diencephalon and to the medullary nucleus raphe magnus in the rat. Neuroscience 42(1, 1991):183-200; BEHBEHANI MM. The role of acetylcholine in the function of the nucleus raphe magnus and in the interaction of this nucleus with the periaqueductal gray. Brain Res 252(2, 1982):299-307]. The periaqueductal gray, raphe nuclei, and locus coeruleus also project to many other sites within the brain, including those that would be excited during ischemia. Therefore, in this aspect of the invention, vagus nerve stimulation during acute stroke or transient ischemic attack has a general neuroprotective, inhibitory effect via its activation of the periaqueductal gray, raphe nuclei, and locus coeruleus.

In particular, the vagus nerve stimulation may be neuroprotective to a part of the brain known as the insula (also known as the insulary cortex, insular cortex, or insular lobe) and its connections with the anterior cingulate cortex (ACC). Neural circuits leading from the vagus nerve to the insula and ACC are shown in FIG. 1A. Protection of the insula is particularly important for stroke patients, because damage to the insula is known to cause symptoms that are typical in stroke patients, involving motor control, hand and eye motor movement, motor learning, swallowing, speech articulation, the capacity for long and complex spoken sentences, sensation, and autonomic functions [ANDERSON TJ, Jenkins I H, Brooks D J, Hawken M B, Frackowiak R S, Kennard C. Cortical control of saccades and fixation in man. A PET study. Brain 117(5, 1994):1073-1084; FINK GR, Frackowiak R S, Pietrzyk U, Passingham R E (April 1997). Multiple nonprimary motor areas in the human cortex. J. Neurophysiol 77 (4, 1997): 2164-2174; SOROS P, Inamoto Y, Martin R E. Functional brain imaging of swallowing: an activation likelihood estimation meta-analysis. Hum Brain Mapp 30(8, 2009):2426-2439; DRONKERS NF. A new brain region for coordinating speech articulation. Nature 384 (6605, 1996): 159-161; ACKERMANN H, Riecker A. The contribution of the insula to motor aspects of speech production: a review and a hypothesis. Brain Lang 89 (2, 2004): 320-328; BOROVSKY A, Saygin A P, Bates E, Dronkers N. Lesion correlates of conversational speech production deficits. Neuropsychologia 45 (11, 2007): 2525-2533; OPPENHEIMER SM, Kedem G, Martin W M. Left-insular cortex lesions perturb cardiac autonomic tone in humans. Clin Auton Res; 6(3, 1996):131-140; CRITCHLEY HD. Neural mechanisms of autonomic, affective, and cognitive integration. J. Comp. Neurol. 493 (1, 2005): 154-166].

Figure 1C:
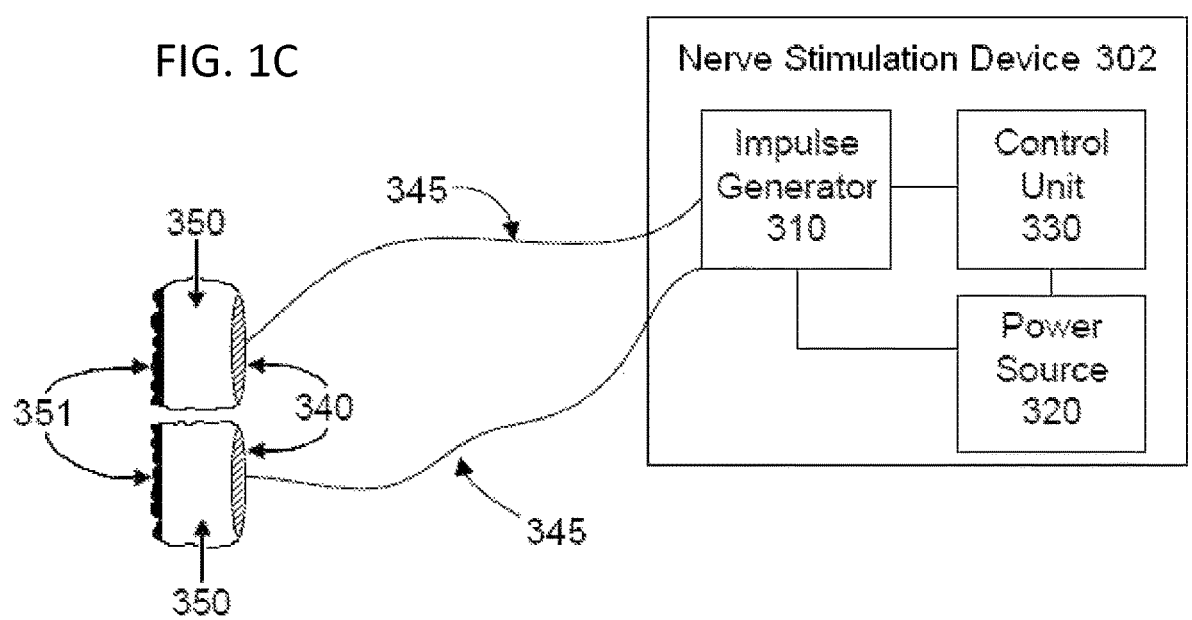
FIG. 1C shows a schematic view of nerve modulating devices according to the present invention, which supply controlled pulses of electrical current to surface electrodes.

Devices of the invention that are used to stimulate a vagus nerve will now be described. An embodiment of the present invention is shown in FIG. 1C, which is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In a preferred embodiment, the same impulse generator 310, power source 320, and control unit 330 may be used for either a magnetic stimulator or the electrode-based stimulator 302, allowing the user to change parameter settings depending on whether magnetic coils or the electrodes 340 are attached.

Although a pair of electrodes 340 is shown in FIG. 1C, in practice the electrodes may also comprise three or more distinct electrode elements, each of which is connected in series or in parallel to the impulse generator 310. Thus, the electrodes 340 that are shown in FIG. 1C represent all electrodes of the device collectively.

The item labeled in FIG. 1C as 350 is a volume, contiguous with an electrode 340, that is filled with electrically conducting medium. The conducting medium in which the electrode 340 is embedded need not completely surround an electrode. The volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In one embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, an electrically conducting or permeable membrane, or a metal piece. In that case, electrical coupling of the stimulator to the patient is ohmic. As shown, the interface may be deformable such that it is form fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's electrodes (or magnetic coils). The signals are selected to be suitable for amelioration of a particular medical condition, when the signals are applied non-invasively to a target nerve or tissue via the electrodes 340. It is noted that nerve stimulating/modulating device 302 may be referred to by its function as a pulse generator. Patent application publications US2005/0075701 and US2005/0075702, both to SHAFER, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from a keyboard, computer mouse, and touchscreen, as well as any externally supplied physiological signals (see FIG. 11), analog-to-digital converters for digitizing externally supplied analog signals (see FIG. 11), communication devices for the transmission and receipt of data to and from external devices such as printers and modems that comprise part of the system, hardware for generating the display of information on monitors or display screens that comprise part of the system, and busses to interconnect the above-mentioned components. Thus, the user may operate the system by typing or otherwise providing instructions for the control unit 330 at a device such as a keyboard or touchscreen and view the results on a device such as the system's computer monitor or display screen, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob, or their touchscreen equivalent. In a section below, an embodiment is also described wherein the stimulator housing has a simple structure, but other components of the control unit 330 are distributed into other devices (see FIG. 7).

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes, as well as the spatial distribution of the electric field that is produced by the electrodes. The rise time and peak energy are governed by the electrical characteristics of the stimulator and electrodes, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurto, Przemystaw Ptonecki, Jacek Starzynski, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, 105 Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

Figure 2A:
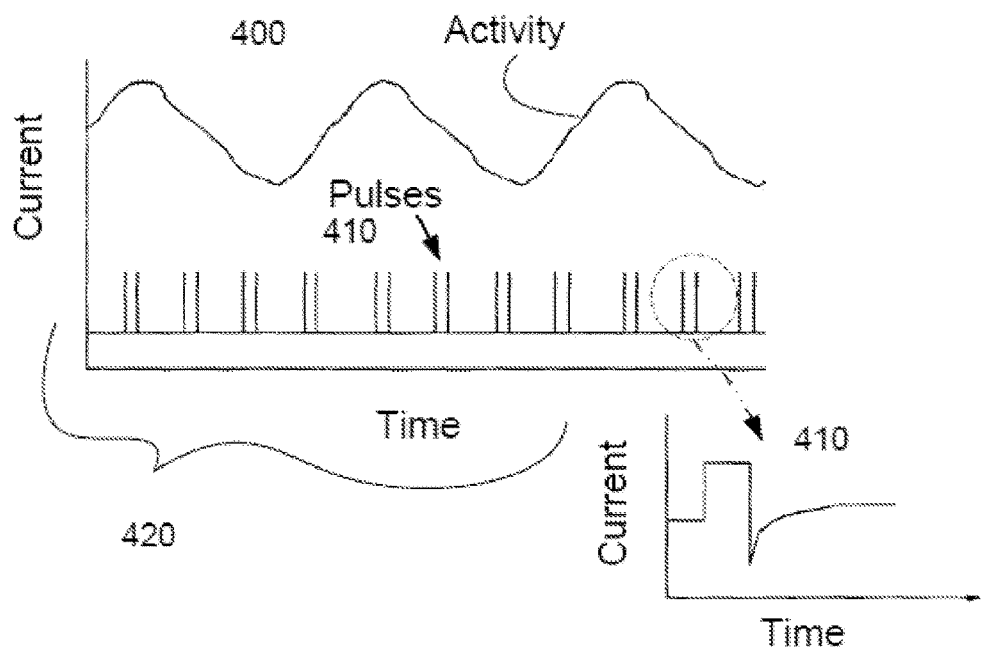
FIG. 2A shows an exemplary electrical voltage/current profile for stimulating and/or modulating impulses that are applied to a nerve according to the present invention.

FIG. 2A illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively produced within the patient by the electrodes (or magnetic coils). As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the electrodes 340 that deliver the stimulating, blocking and/or modulating impulse 410 to the nerve. Nerve stimulating/modulating device 302 may be externally powered and/or recharged or may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes, the device disclosed in patent publication No. US2005/0216062 may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bio-electromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated, as well as the outputs of various sensors which sense prevailing conditions prevailing in this substance, whereby the user of the system can manually adjust the signal, or have it automatically adjusted by feedback, to provide an electrical stimulation signal of whatever type the user wishes, who can then observe the effect of this signal on a substance being treated.

The stimulating and/or modulating impulse signal 410 preferably has a frequency, an amplitude, a duty cycle, a pulse width, a pulse shape, etc. selected to influence the therapeutic result, namely, stimulating and/or modulating some or all of the transmission of the selected nerve. For example, the frequency may be about 1 Hz or greater, such as between about 15 Hz to 100 Hz, preferably between about 15-50 Hz and more preferably between about 15-35 Hz. In an exemplary embodiment, the frequency is 25 Hz. The modulation signal may have a pulse width selected to influence the therapeutic result, such as about 1 microseconds to about 1000 microseconds, preferably about 100-400 microseconds and more preferably about 200-400 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts, preferably between about 1-20 volts and more preferably between about 2-12 volts.

An objective of the disclosed stimulators is to provide both nerve fiber selectivity and spatial selectivity. Spatial selectivity may be achieved in part through the design of the electrode (or magnetic coil) configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in patent number U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Figure 2B:
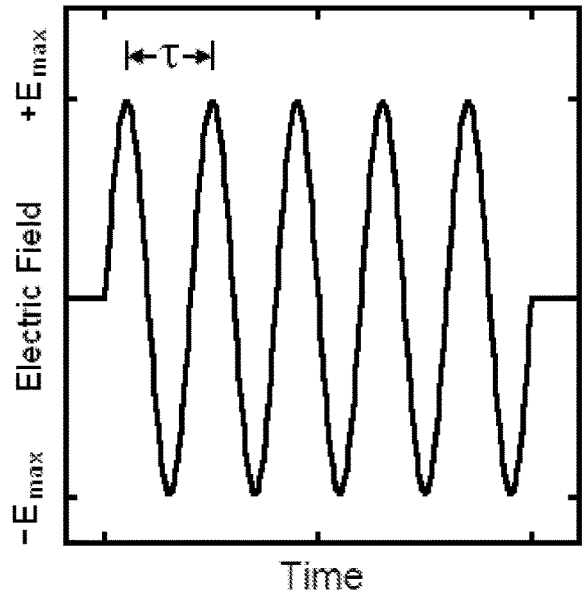
FIG. 2B illustrates an exemplary bursting electrical waveform for stimulating and/or modulating a nerve according to the present invention.
Figure 2C:
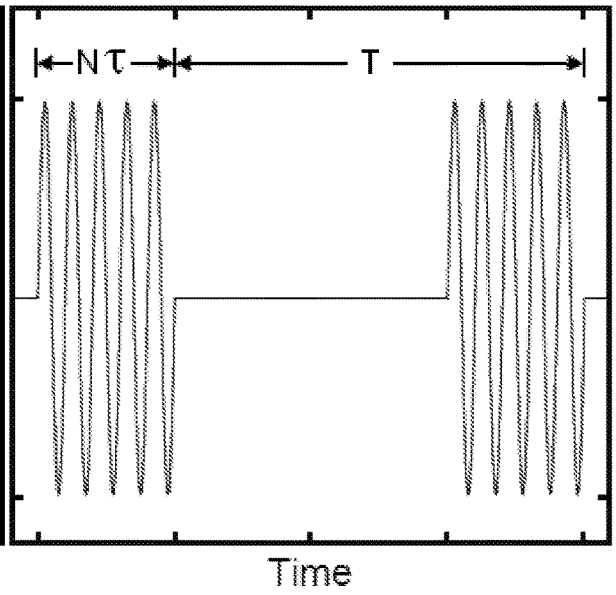
FIG. 2C illustrates two successive bursts of the waveform of FIG. 2B.

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340, entitled Stimulation design for neuromodulation, to De Ridder]. However, bursts of sinusoidal pulses are a preferred stimulation waveform, as shown in FIGS. 2B and 2C. As seen there, individual sinusoidal pulses have a period of T, and a burst consists of N such pulses. This is followed by a period with no signal (the inter-burst period). The pattern of a burst followed by silent inter-burst period repeats itself with a period of T. For example, the sinusoidal period T may be between about 50-1000 microseconds (equivalent to about 1-20 KHz), preferably between about 100-400 microseconds (equivalent to about 2.5-10 KHz), more preferably about 133-400 microseconds (equivalent to about 2.5-7.5 KHZ) and even more preferably about 200 microseconds (equivalent to about 5 KHz); the number of pulses per burst may be N=1-20, preferably about 2-10 and more preferably about 5; and the whole pattern of burst followed by silent inter-burst period may have a period T comparable to about 10-100 Hz, preferably about 15-50 Hz, more preferably about 25-35 Hz and even more preferably about 25 Hz (a much smaller value of T is shown in FIG. 2E to make the bursts discernable). When these exemplary values are used for T and τ, the waveform contains significant Fourier components at higher frequencies (1/200 microseconds=5000/sec), as compared with those contained in transcutaneous nerve stimulation waveforms, as currently practiced.

The above waveform is essentially a 1-20 KHz signal that includes bursts of pulses with each burst having a frequency of about 10-100 Hz and each pulse having a frequency of about 1-20 KHz. Another way of thinking about the waveform is that it is a 1-20 KHz waveform that repeats itself at a frequency of about 10-100 Hz. Applicant is unaware of such a waveform having been used with vagus nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein.

Furthermore, the signal used for muscle strengthening may be other than sinusoidal (e.g., triangular), and the parameters τ, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10(1989):187-191; Alex R WARD, Nataliya Shkuratova. Russian Electrical Stimulation: The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008): 1167-1176; Alex R WARD. Electrical Stimulation Using Kilohertz-Frequency Alternating Current. Physical Therapy 89 (2, 2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2B and 2C may have an $E_{max}$ value of 17 V/m, which is sufficient to stimulate the nerve but is significantly lower than the threshold needed to stimulate surrounding muscle.

Figure 11:
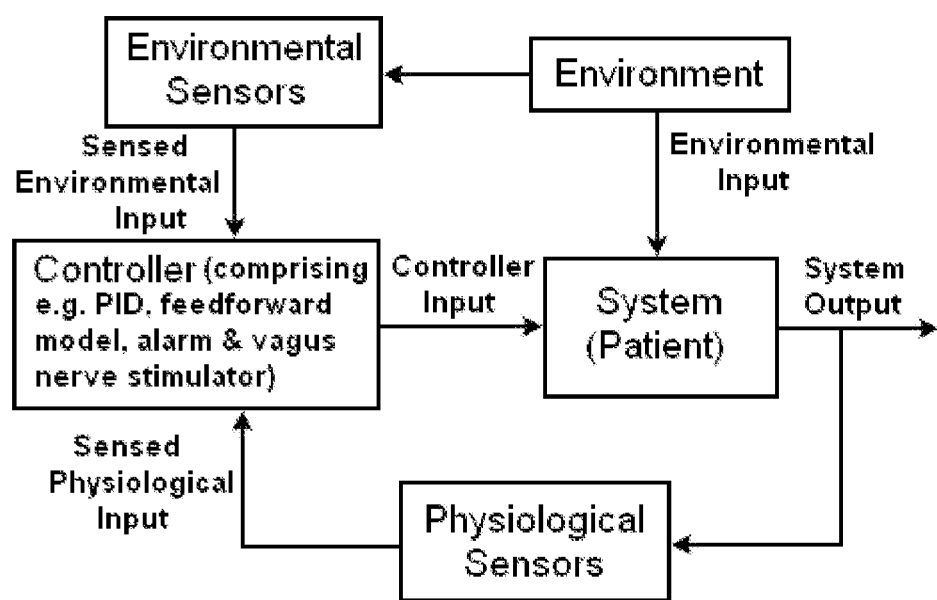
FIG. 11 illustrates connections between the controller and controlled system according to the present invention, their input and output signals, and external signals from the environment.

The use of feedback to generate the modulation signal 400 may result in a signal that is not periodic, particularly if the feedback is produced from sensors that measure naturally occurring, time-varying aperiodic physiological signals from the patient (see FIG. 11). In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128; W Alan C MUTCH, M Ruth Graham, Linda G Girling and John F Brewster. Fractal ventilation enhances respiratory sinus arrhythmia. Respiratory Research 2005, 6:41, pp. 1-9].

So, in one embodiment of the present invention, the modulation signal 400, with or without feedback, will stimulate the selected nerve fibers in such a way that one or more of the stimulation parameters (power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

In another embodiment, devices in accordance with the present invention are provided in a "pacemaker" type form, in which electrical impulses 410 are generated to a selected region of the nerve by a stimulator device on an intermittent basis, to create in the patient a lower reactivity of the nerve.

The electrodes of the invention are applied to the surface of the neck, or to some other surface of the body, and are used to deliver electrical energy non-invasively to a nerve. Embodiments of the present invention may differ with regard to the number of electrodes that are used, the distance between electrodes, and whether disk or ring electrodes are used. In preferred embodiments of the method, one selects the electrode configuration for individual patients, in such a way as to optimally focus electric fields and currents onto the selected nerve, without generating excessive currents on the surface of the skin. This tradeoff between focality and surface currents is described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174]. Although DATTA et al. are addressing the selection of electrode configuration specifically for transcranial current stimulation, the principles that they describe are applicable to peripheral nerves as well [RATTAY F. Analysis of models for extracellular fiber stimulation. IEEE Trans. Biomed. Eng. 36 (1989): 676-682].

A preferred embodiment of an electrode-based stimulator is shown in FIG. 3. As shown, the stimulator comprises a smartphone (31) with its back cover removed and and joined to a housing (32) that comprises a pair of electrode surfaces (33) along with circuitry (not shown) to control and power the electrodes and interconnect with the smartphone. The electrode surface (33) in FIG. 3 corresponds to item 351 in FIG. 1. FIG. 3A shows the side of the smartphone (31) with a touch-screen. FIG. 3B shows the housing of the stimulator (32) joined to the back of the smartphone. Portions of the housing lie flush with the back of the smartphone, with windows to accommodate smartphone components that are found on the original back of the smartphone. Such components may also be used with the stimulator, e.g., the smartphone's rear camera (34), flash (35) and speaker (36). Other original components of the smartphone may also be used, such as the audio headset jack socket (37) and multi-purpose jack (38). Note that the original components of the smartphone shown in FIG. 3 correspond to a Samsung Galaxy smartphone, and their locations may be different for embodiments that use different smartphone models.

FIG. 3C shows that several portions of the housing (32) protrude towards the back. The two electrode surfaces (33) protrude so that they may be applied to the skin of the patient. The stimulator may be held in place by straps or frames or collars, or the stimulator may be held against the patient's body by hand. Other embodiments of the invention may comprise a single such electrode surface or more than two electrode surfaces.

A dome (39) also protrudes from the housing, so as to allow the device to lie more or less flat on a table when supported also by the electrode surfaces. The dome also accommodates a relatively tall component that may lie underneath it, such as a battery. Alternatively, the stimuluation device may be powered by the smartphone's battery. If the battery under the dome is rechargeable, the dome may contain a socket (41) through which the battery is recharged using a jack that is inserted into it, which is, for example, attached to a power cable from a base station (described below). The belly (40) of the housing protrudes to a lesser extent than the electrodes and dome. The belly accommodates a printed circuit board that contains electronic components within the housing (not shown), as described below.

Generally, the stimulator is designed to situate the electrodes of the stimulator (340 in FIG. 1) remotely from the surface of the skin within a chamber, with conducting material (350 in FIG. 1) placed in a chamber between the electrode and the exterior component of the stimulator head that contacts the skin (351 in FIG. 1). One of the novelties of this design is that the stimulator, along with a correspondingly suitable stimulation waveform (see FIG. 2), shapes the electric field, producing a selective physiological response by stimulating that nerve, but avoiding substantial stimulation of nerves and tissue other than the target nerve, particularly avoiding the stimulation of nerves that produce pain. The shaping of the electric field is described in terms of the corresponding field equations in co-pending, commonly assigned application US20110230938 (application Ser. No. 13/075,746), entitled Devices and methods for non-invasive electrical stimulation and their use for vagal nerve stimulation on the neck of a patient, to SIMON et al., which is hereby incorporated by reference.

In certain embodiments, the disc interface 351 actually functions as the electrode and the screw 340 is simply the output connection to the signal generator electronics. In this embodiment, electrically conductive fluid or gel is positioned between the signal generator and the interface or electrode 351. In this embodiment, the conductive fluid filters out or eliminates high frequency components from the signal to smooth out the signal before it reaches the electrode (s) 351. When the signal is generated, power switching and electrical noise typically add unwanted high frequency spikes back into the signal. In addition, the pulsing of the sinusoidal bursts may induce high frequency components in the signal. By filtering the signal just before it reaches the electrodes 351 with the conductive fluid, a smoother, cleaner signal is applied to the patient, thereby reducing the pain and discomfort felt by the patient and allowing a higher amplitude to be applied to the patient. This allows a sufficiently strong signal to be applied to reach a deeper nerve, such as the vagus nerve, without causing too much pain and discomfort to the patient at the surface of their skin.

In other embodiments, a low-pass filter may be used instead of the electrically conductive fluid to filter out the undesirable high frequency components of the signal. The low-pass filter may comprise a digital or active filter or simply two series resistors and a parallel capacitor placed between the signal generator and the electrode/interface.

Figure 4A:
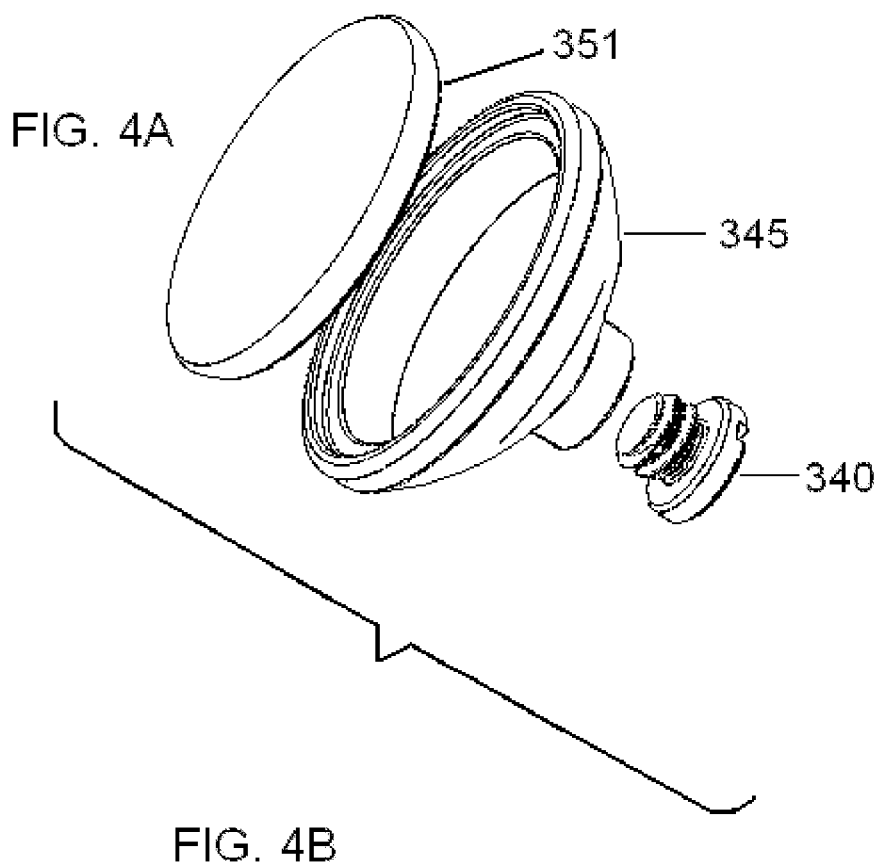
FIG. 4A illustrates an exploded view of an electrode assembly according to one embodiment of the present invention.
Figure 4B:
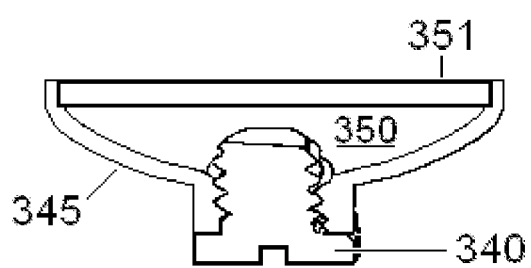
FIG. 4B illustrates an assembled view of the electrode assembly shown in FIG. 4A.

The electrode surface (33) was shown in FIG. 3C as being roughly hemispherical so that as the electrode surface is pressed into the patient's skin, the surface area of skin contact would increase. However, in other designs of the electrode surface (corresponding to 351 in FIG. 1), the electrode surface may be flat. Such an alternate design is shown in FIG. 4. As shown in FIG. 4A, the electrode surface (351) comprises a metal (e.g., stainless steel) disc that fits into the top of a non-conducting (e.g., plastic) chamber (345). At the other end of the chamber, a threaded port accepts a metal screw that serves as the actual electrode (340). A wire will be attached to the screw, connecting it to impulse generating circuitry. The assembled components are shown in FIG. 4B, which also shows the location of an electrically conducting material (350) within the chamber, such as an electrolyte solution or gel, that allows the electrode (340) to conduct current to the external electrode surface (351).

In one embodiment, the signal waveform (FIG. 2) that is to be applied to electrodes of the stimulator is initially generated in a component of the impulse generator (310 in FIG. 1) that is exterior to, and remote from, the mobile phone housing. The mobile phone preferably includes a software application that can be downloaded into the phone to receive, from the external control component, a wirelessly transmitted waveform, or to receive a waveform that is transmitted by cable, e.g., via the multi-purpose jack 38 in FIG. 3. If the waveforms are transmitted in compressed form, they are preferably compressed in a lossless manner, e.g., making use of FLAG (Free Lossless Audio Codec). Alternatively, the downloaded software application may itself be coded to generate a particular waveform that is to be applied to the electrodes (340 in FIG. 1C) and subsequently conveyed to the external interface of the electrode assembly (351 in FIGS. 1C and 33 in FIG. 3). In yet another embodiment, the software application is not downloaded from outside the device, but is instead available internally, for example, within read-only-memory that is present within the housing of the stimulator (32 in FIGS. 3B and 3C).

In one embodiment, the waveform is first conveyed by the software application to contacts within the phone's speaker output or the earphone jack socket (37 in FIG. 3B), as though the waveform signal were a generic audio waveform. That pseudo-audio waveform will generally be a stereo waveform, representing signals that are to be applied to the "left" and "right" electrodes. The waveform will then be conveyed to the housing of the stimulator (32 in FIGS. 3B and 3C), as follows. The housing of the stimulator may have an attached dangling audio jack that is plugged into the speaker output or the earphone jack socket 37 whenever electrical stimulation is to be performed, or the electrical connection between the contacts of the speaker output or the earphone jack socket and the housing of the stimulator may be hard-wired. In either case, electrical circuits on a printed circuit board located under the belly of the housing (40 in FIG. 3C) of the stimulator may then shape, filter, and/or amplify the pseudo-audio signal that is received via the speaker output or earphone jack socket. A power amplifier within the housing of the stimulator may then drive the signal onto the electrodes, in a fashion that is analogous to the use of an audio power amplifier to drive loudspeakers. Alternatively, the signal processing and amplification may be implemented in a separate device that can be plugged into sockets on the phone and/or housing of the stimulator (32 in FIGS. 3B and 3C), to couple the software application and the electrodes.

In addition to passing the stimulation waveform from the smartphone to the stimulator housing as described above, the smartphone may also pass control signals to the stimulator housing. Thus, the stimulation waveform may generally be regarded as a type of analog, pseudo-audio signal, but if the signal contains a signature series of pulses signifying that a digital control signal is about to be sent, logic circuitry in the stimulator housing may then be set to decode the series of digital pulses that follows the signature series of pulses, analogous to the operation of a modem.

Many of the steps that direct the waveform to the electrodes, including steps that may be controlled by the user via the touchscreen (31 in FIG. 3A), are implemented in the above-mentioned software application. By way of example, the software application may be written for a phone that uses the Android operating system. Such applications are typically developed in the Java programming language using the Android Software Development Kit (SDK), in an integrated development environment (IDE), such as Eclipse [Mike WOLFSON. Android Developer Tools Essentials. Sebastopol, Calif.: O'Reilly Media Inc., 2013; Ronan SCHWARZ, Phil Duston, James Steele, and Nelson To. The Android Developer's Cookbook. Building Applications with the Android SDK, Second Edition. Upper Saddle River, N.J.: Addison-Wesley, 2013; Shane CONDER and Lauren Darcey. Android Wireless Application Development, Second Edition. Upper Saddle River, N.J.: Addison-Wesley, 2011; Jerome F. DIMARZIO. Android—A Programmer's Guide. New York: McGraw-Hill. 2008. pp. 1-319]. Application programming interfaces (APIs) that are particularly relevant to the audio features of such an Android software application (e.g., MediaPlayer APIs) are described by: Android Open Source Project of the Open Handset Alliance. Media Playback, at web domain developer.android.com with subdomain /guide/topics/media/, Jul. 18, 2014. Those APIs are also particularly relevant to the invention's use of the smartphone camera capabilities, as described below. Additional components of the software application are available from device manufacturers [Samsung Mobile SDK, at web domain developer.samsung.com with subdomain /samsung-mobile-sdk, Jul. 18, 2014].

In certain embodiments, the stimulator and/or smartphone will include a user control, such as a switch or button, that disables/enables the stimulator. Preferably, the switch will automatically disable all smartphone functions when the stimulator is enabled (and vice versa). This ensures that the medical device functionality of the smartphone is completely segregated from the rest of the phone's functionality. In preferred embodiments, the switch will be password-controlled such that only the patient/owner of the stimulator/phone will be able to enable the stimulator functionality. In one such embodiment, the switch will be controlled by a biometric scan (e.g., fingerprint, optical scan or the like) such that the stimulator functionality can only be used by the patient. This ensures that only the patient will be able to use the prescribed therapy in the event the phone is lost or stolen.

The stimulator and/or phone will also include software that allows the patient to order more therapy doses over the internet (discussed in more detail below in connection with the docking station). The purchase of such therapy doses will require physician authorization through a prescription or the like. To that end, the software will preferably include an authorization code that should be entered in order for the patient to download authorization for more therapies. Without such authorization, the stimulator will be disabled and will not deliver therapy.

Although the device shown in FIG. 3 is an adapted commercially available smartphone, it is understood that in some embodiments, the housing of the stimulator may also be joined to and/or powered by a wireless device that is not a phone (e.g., Wi-Fi enabled device). Alternatively, the stimulator may be coupled to a phone or other Wi-Fi enabled device through a wireless connection for exchanging data at short distances, such as Bluetooth or the like. In this embodiment, the stimulator housing is not attached to the smartphone and, therefore, may comprise a variety of other shapes and sizes that are convenient for the patient to carry in his or her purse, wallet or pocket.

In other embodiments, the stimulator housing may be designed as part of a protective or decorative case for the phone that can be attached to the phone, similar to standard phone cases. In one such embodiment, the stimulator/case may also include additional battery life for the phone and may include an electrical connection to the phone's battery to recharge the battery (e.g., part of a Mophie® or the like). This electrical connection may also be used to couple the smartphone to the stimulator.

Reproducibility of the effects of electrical stimulation of a nerve, such as a vagus nerve, depends in part on one's ability to position the electrode surfaces to an optimal location on the patient's skin during successive stimulation sessions. The present invention includes methods for repositioning the stimulation device during subsequent sessions. The methods that are disclosed below involve initially determining an optimal position for the stimulator by imaging the nerve with ultrasound, then marking that position on the patient's skin with spots of dyes ("tattoos"), and eventually repositioning the stimulation device in conjunction with imaging the spots of dyes with the rear camera of the smartphone.

The preferred ultrasound transducer/probe used to image the vagus nerve (or other stimulated nerve) is a "hockey stick" style of probe, so-called because of its shape, which is commercially available from most ultrasound machine manufacturers. As an example, the Hitachi Aloka UST-536 19 mm Hockey Stick style Transducer for superficial viewing has a frequency range of 6-13 MHz, a scan angle of 90 degrees, and a probe surface area of approximately 19 mm×4 mm (Hitachi Aloka Medical America, 10 Fairfield Boulevard, Wallingford Conn. 06492). The transducer connects to the ultrasound machine that displays the anatomical structures that lie under the transducer.

The neck skin location for electrically stimulating the vagus nerve is determined preliminarily by positioning an ultrasound probe at the location where the center of each smartphone electrode will be placed (33 in FIG. 3), such that the vagus nerve appears in the center of the ultrasound image [KNAPPERTZ VA, Tegeler C H, Hardin S J, McKinney W M. Vagus nerve imaging with ultrasound: anatomic and in vivo validation. Otolaryngol Head Neck Surg 118(1, 1998): 82-5]. Once that location has been found for an electrode, temporary spots are marked on the patient's neck with ink to preserve knowledge of the location and orientation of the ultrasound probe, through stencil holes that are attached on both sides of the shorter dimension of the ultrasound probe. When the preferred ultrasound location on the skin for each electrode has been ascertained, the interpolated optimal location under the center of the rear camera is then marked (tattooed) on the patient's skin with one of the more permanent fluorescent dyes that are described below. The interpolation may be performed using a long, rectangular stencil with several holes, wherein holes near the ends of the stencil are aligned with the temporary spots that had been marked for the electrode locations, and wherein a central hole of the stencil is used to apply the permanent fluorescent dye to a location that will lie under the smartphone camera. Ordinarily two or more adjacent fluorescent dye locations are marked, such that if the stencil is subsequently aligned centrally over the fluorescent spots on the skin, the end holes of the stencil would also align with the temporary spot locations that had been marked to record the ultrasound probe location matching electrode locations.

It is understood that any non-toxic dye may be used to permanently mark a location on the patient's skin. However, the preferred type of permanent dye is a fluorophore that is only visible or detectable as a spot on the patient's neck when one shines non-visible light upon it, e.g., ultraviolet light ("blacklight") or infrared light. This is because the patient is thereby spared the embarrassment of explaining why there would otherwise be a visible spot mark on his or her neck, and also because such a dye is suitable for showing where to place the stimulator irrespective of whether the patient is dark-skinned or light-skinned. Another method, which is to attempt to match the color of the dye to the patient's flesh color, would be generally impractical. Marking with a fluorescent dye (e.g., from ordinary highlighting pens) has been performed previously by surgeons and radiologists to outline where a procedure is to be performed. However, the marking in the present invention is different in that it is intended to be used repeatedly by a patient alone for device positioning at small discrete spots [DAVID, J. E., Castle, S. K. B., and Mossi, K. M. Localization tattoos: an alternative method using fluorescent inks. Radiation Therapist 15(2006):1-5; WATANABE M, Tsunoda A, Narita K, Kusano M, Miwa M. Colonic tattooing using fluorescence imaging with light-emitting diode-activated indocyanine green: a feasibility study. Surg Today 39(3, 2009):214-218].

Once the position-indicating fluorescent spots have been applied on the patient's skin as described above, they may fade and eventually disappear as the stained outer surface of the patient's skin exfoliates. The exfoliation will occur naturally as the patient washes his or her neck and may be accelerated by mechanical (e.g., abrasive) or chemical methods that are routinely used by cosmetologists. Before the spot disappears, the patient or a family member may reapply the dye/fluorophor to the same spot while observing it with ultraviolet or infrared light (as the case may be), by masking the skin outside the spot and then applying new dye solution directly with a cotton swab. Viewing of the fluorescence that is excited by ultraviolet light can be done with the naked eye because it comprises blue light, and viewing of fluorescence that is excited by infrared light can be done with a conventional digital camera after removing the camera's IR-blocking filter. For some cameras, removal of an IR-blocking filter may not be necessary (e.g., those that can perform retinal biometric scans). Some of the infrared fluorescent dyes may also be faintly visible to the naked eye even under room light, depending on their concentration (e.g., indocyanine green).

Alternatively, a semi-permanent or permanent tattooing method of marking or re-marking the fluorescent spots may be used by a licensed professional tattooer, by injecting the dye/fluorophor into an outer skin layer or deeper into the skin [Maria Luisa Perez-COTAPOS, Christa De Cuyper, and Laura Cossio. Tattooing and scarring: techniques and complications. In: Christa de Cuyper and Maria Luisa Cotapos (Eds.). Dermatologic Complications with Body Art: Tattoos, Piercings and Permanent Make-Up. Berlin and London: Springer, 2009, pp. 31-32].

Many dyes can be used for the ultraviolet marking, but the most convenient ones for skin-surface marking are those that are commercially available to hand-stamp attendees of events. For tattooing applications, ultraviolet-absorbing injectable fluorophores are commercially available that are encapsulated within microspheres [Technical sheet for Opticz UV Blacklight Reactive Blue Invisible Ink. 2013. Blacklight.com, 26735 W Commerce Dr Ste 705, Volo, Ill. 60073-9658; Richard P. HAUGLAND. Fluorophores excited with UV light. Section 1.7 In: The Molecular Probes Handbook: A Guide to Fluorescent Probes and Labeling Technologies, 11th Edition, 2010. Molecular Probes/Life Technologies. 4849 Pitchford Ave., Eugene, Oreg. 97402. pp. 66-73; Technical sheet for BIOMATRIX System. 2013. NEWWEST Technologies, Santa Rosa Calif. 95407-0286].

Many dyes can also be used for the infrared marking, their major advantage being that auto-fluorescence from human skin or tissue generally does not interfere with detection of their fluorescence. In fact, the infrared fluorophores may be imaged up to about two centimeters under the skin. Examples of such dyes are indocyanine green and Alexa Fluor 790. Quantum dots may also be used to generate infrared fluorescence, advantages of which are that they are very stable and very brightly fluorescent. They may also be encapsulated in microspheres for purposes of tattooing. Quantum dots may also be electroluminescent, such that the electric field and currents produced by the stimulator might alone induce the emission of infrared light from the quantum dots [Richard P. HAUGLAND. Alexa Fluor Dyes Spanning the Visible and Infrared Spectrum—Section 1.3; and Qdot Nanocrystals—Section 6.6. In: The Molecular Probes Handbook: A Guide to Fluorescent Probes and Labeling Technologies, 11th Edition, 2010. Molecular Probes/Life Technologies. 4849 Pitchford Ave., Eugene, Oreg. 97402; GRAVIER J, Navarro F P, Delmas T, Mittler F, Couffin A C, Vinet F, Texier I. Lipidots: competitive organic alternative to quantum dots for in vivo fluorescence imaging. J Biomed Opt. 16(9, 2011):096013; ROMOSER A, Ritter D, Majitha R, Meissner K E, McShane M, Sayes C M. Mitigation of quantum dot cytotoxicity by microencapsulation. PLoS One. 6(7, 2011):e22079:pp. 1-7; Andrew M. SMITH, Michael C. Mancini, and Shuming Nie. Second window for in vivo imaging. Nat Nanotechnol 4(11, 2009): 710-711].

Figure 8:
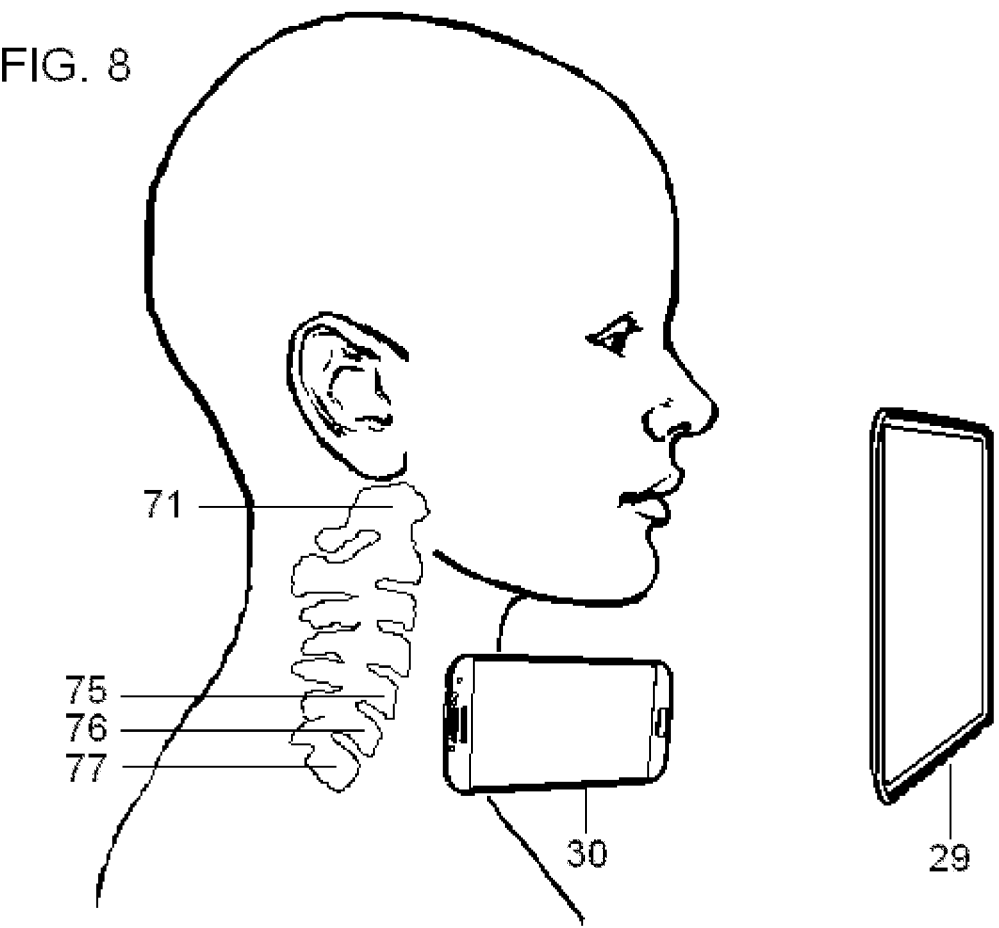
FIG. 8 illustrates the approximate position of the stimulator according one embodiment of the present invention, when used to stimulate the right vagus nerve in the neck of an adult patient.
Figure 10:
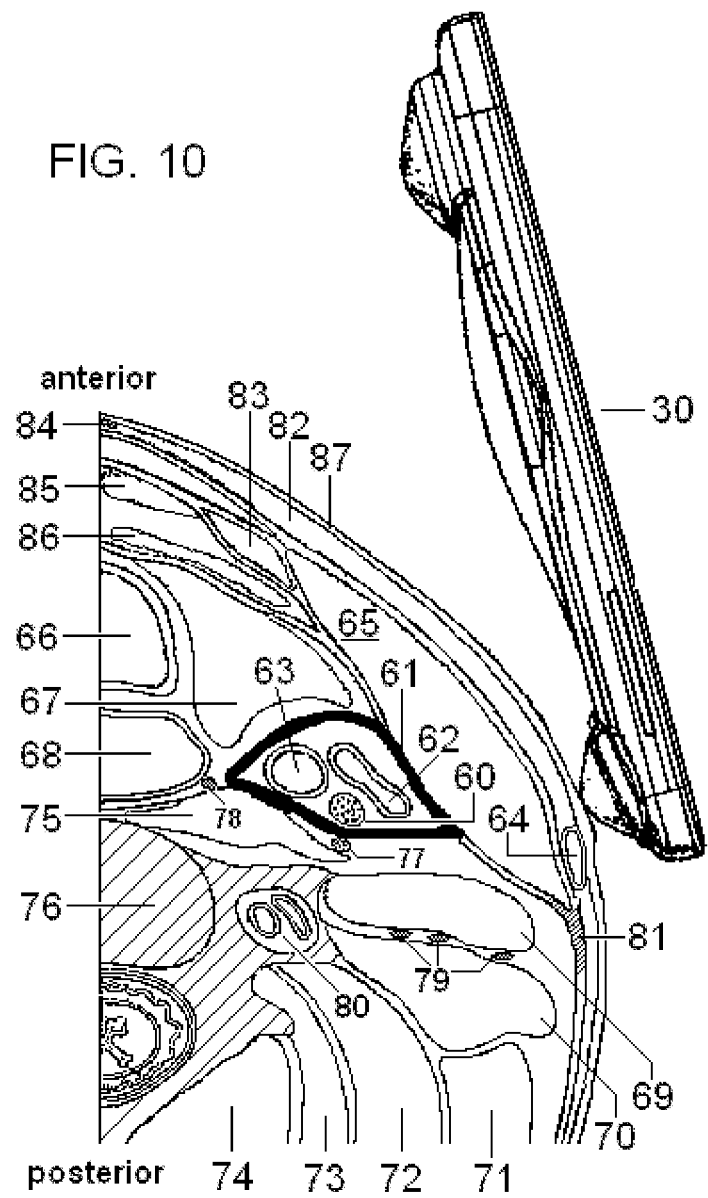
FIG. 10 illustrates the stimulator according one embodiment of the present invention, when positioned to stimulate a vagus nerve in the patient's neck, wherein the stimulator is applied to the surface of the neck in the vicinity of the identified anatomical structures.

Once the patient is ready to apply the stimulator to the neck (as shown in FIGS. 8 and 10), he or she will place a snap-in optical attachment (50 in FIG. 5C) on the back of the smartphone, at a location on top of the rear camera (34 in FIG. 3B) and camera flash (35 in FIG. 3B), and between the electrode surfaces (33 in FIGS. 3 and 5). The purpose of the optical attachment is to facilitate optimal positioning of the electrodes, by forming a camera image of fluorescence from the spots of dye that had been placed in or under the patient's skin.

Once the snap-in optical attachment is in place, apertures are formed between the optical attachment and the rear camera/flash, as indicated by 34' and 35' in FIGS. 5A, 5B, and 5C. The optical elements shown in FIGS. 5A and 5B that are situated above the apertures are present in the smartphone, and the optical elements situated below the apertures in those figures are components of the snap-in optical attachment. The optical elements in the smartphone include a flash, which is a light-emitting diode (LED) 43 that may be programmed to provide illumination while taking a photograph (or may be even be programmed to serve as a flashlight). Without the snap-in optical attachment, light reflected back from the LED-illuminated objects would be imaged by a lens 44 that is internal to the smartphone. When the snap-in optical attachment is in place, a macro lens (56 in FIGS. 5A, 5B, and 5C) within the attachment allows for the imaging of close objects, which in this application will be fluorescence 55 emanating from the fluorescent spot of dye 59, on or under the patient's skin 58. As an example, the macro lens may be similar to ones sold by Carson Optical [LensMag™—model ML-415, Carson Optical, 35 Gilpin Avenue, Hauppauge, N.Y. 11788].

In order to produce fluorescence from the fluorescent dye in the patient's skin, the dye should be illuminated with wavelengths corresponding to peaks in its excitation spectrum. In the preferred embodiment of the invention, infrared illumination causes the dye (e.g., indocyanine green) to fluoresce at a wavelength greater than 820 nm, and the LED may be used to illuminate the dye at its excitation wavelength near 760 or 785 nm. Because the LED found in some smartphone cameras may only generate light predominantly in the visible range (400-700 nm), the optical components shown in FIG. 5A are used to shift the light towards the preferred infrared excitation wavelengths. As light leaves the LED 43 of the flash unit, it first encounters a dichroic mirror 51 that passes light with a wavelength less than 700 nm (visible light) and reflects light with wavelengths greater than 700 nm (infrared light). The light passing through the dichroic mirror then encounters a film of phosphorescent material 52 that absorbs the visible light and emits phosphorescent infrared light with a peak in the range of about 760 to 785 nm [Haifeng XIANG, Jinghui Cheng, Xiaofeng Ma, Xiangge Zhou and Jason Joseph Chruma. Near-infrared phosphorescence: materials and applications. Chem. Soc. Rev. 42(2013): 6128-6185]. If the phosphorescent infrared light is emitted back towards the LED, then the dichroic mirror 51 reflects the phosphorescence back into a chamber 53, where it joins phosphorescence that is emitted in the direction away from the LED. The chamber 53 is coated internally with a reflective material such as silver, so that the phosphorescence may undergo multiple reflections from the silver or from the dichroic mirror 51, until it eventually emerges as light from a slit 54 that is directed towards the spots on the patient's skin. Similarly, visible light that passes through the phosphorescent layer 52 without generating phosphorescence may also undergo multiple reflections from the silver coating until it encounters the phosphorescent layer 52 again, which this time may produce phosphorescence, or it may pass back through the dichroic mirror and be lost (along with first-pass visible light that is backscattered from the phosphorescent layer), unless it is reflected back through the dichroic mirror 51 from the surface of the LED. Some of the visible light that enters the chamber 53 may also emerge as light from the slit 54. However, the visible light emerging from the slit does not have wavelengths needed to produce fluorescence 55 from the infrared dye 59 in the patient's skin 58. Furthermore, any of the visible light that emerges from the slit and eventually makes its way through the macro lens 56 would be blocked by a filter 57 that passes only light having a wavelength greater than about 800 nm. Thus, the filter 57 will block not only any visible light from the LED, but also the excitation infrared wavelengths less than about 780 nm that are produced by the phosphorescent layer 52. The light that does pass through the filter 57 will be mostly fluorescence from the spot of dye 59, and that fluorescence will be imaged by the lens 44 onto the light-sensitive elements in the smartphone's rear camera, thereby producing an image of the fluorescent spot.

Note that the foregoing description presumes that there is a gap between the macro lens 56 and the patient's skin 58, such that the excitation wavelengths of light may pass under the macro lens to wherever the infrared dye 59 may be located. This would generally be the case because the height of the electrode surfaces (33' in FIGS. 5A and 5B) prevent the macro lens 56 from reaching the surface of the patient's skin. However, even if the macro lens 56 were pressed all the way to the surface of the skin, a spot of fluorescent dye 59 could still be excited by the light if it had been injected deeper than the surface of the skin. This is because infrared light may penetrate up to about 2 cm through the skin.

In the event that the LED 43 produces light with wavelengths that are suitable for excitation of the fluorescent dye, then the phosphorescent layer 52 that is shown in FIG. 5A is not necessary. For example, this would be the case if the LED 43 produces sufficient light with wavelengths around 760 nm to 785 nm, which would excite the infrared dye indocyanine green. This would also be the case if one were exciting a dye that is excited with light in the ultraviolet and violet range, producing blue fluorescence. In those cases, the snap-in optical attachment shown in FIG. 5B would be more appropriate. As shown there, a filter 51' would pass light with wavelengths only in the range that excites the fluorophore, and it therefore would not pass the wavelengths of fluorescence that are emitted by the fluorophore (or other confounding wavelengths). The excitation illumination will then enter a chamber 53' with reflective internal surfaces, such that the excitation light will appear as light emanating from a slit 54', which is directed towards the fluorophore spot 59 in or under the patient's skin 58. That excitation illumination will then cause the fluorophore spot in the patient's skin to emit fluorescent light 55, which will be collected by the macro lens 56. Light corresponding to the excitation wavelengths will also be collected by the macro lens 56, but a filter 57' will block the excitation wavelengths of light and pass only the fluorescence. The fluorescence will then be collected by the smartphone's lens 44 and be imaged onto the photosensitive material of the smartphone's camera, thereby producing an image of the fluorescent spot in or under the patient's skin.

During initial testing of the stimulator on the patient, the appropriate snap-in optical attachment will be in place (as described above), and the smartphone's camera will be turned on, while electrical impulses from the electrode surfaces 33 are applied to the patient's skin. If the electrodes are near their optimal position on the patient's skin, the fluorescent spots that had been applied to the patient's skin should then appear in an image produced by the smartphone's camera, viewable on the screen of the smartphone (31 in FIG. 3). The electrodes may then be slightly translated, rotated, and depressed into the patient's skin, until a maximum therapeutic response is achieved. Methods for evaluating the response at a particular stimulator setting were disclosed in a commonly assigned, co-pending application U.S. Ser. No. 13/872,116 (publication No. US20130245486), entitled DEVICES AND METHODS FOR MONITORING NON-INVASIVE VAGUS NERVE STIMULATION, to SIMON et al, which is hereby incorporated by reference. Once the maximum therapeutic position of the electrodes has been decided, a reference image of the fluorescent spots will then be recorded at that position and saved in the memory of the smartphone for future reference.

During subsequent sessions when the patient applies the stimulator to his or her skin, the appropriate snap-in optical attachment will also be in place, and the smartphone's camera will be turned on, while electrical impulses from the electrode surfaces 33 are applied to the patient's skin. The fluorescent spots that had been applied to the patient's skin should then also appear in an image produced by the smartphone's camera, viewable on the screen of the smartphone (31 in FIG. 3). By superimposing the currently viewed image of the fluorescent spots onto the previously recorded reference image of the fluorescent spots, one may then ascertain the extent to which the current position, orientation, and depth-into-the-skin of the electrode surfaces match the previously recorded optimal reference position. This is illustrated in FIG. 6, which shows the currently imaged fluorescent spots and the superimposed reference spots, as well as the rotation and translation needed to align the former onto the latter spots. Instead of superimposing images of the current and reference images of the spots, one may also subtract the two images, pixel-by-pixel, and display the absolute value of the difference. In that case, optimal positioning of the electrode surfaces would occur when the reference image approximately nulls the current image. The sum of the pixel values in the nulled image may then be used as an index of the extent to which the current and reference images coincide. The control unit of the stimulator may also be configured to disable electrical stimulation of the vagus nerve unless a pre-determined cutoff in the index of alignment of the images has been achieved. For example, use of such a fluorescent spot alignment index may be used to ensure that the patient is attempting to stimulate the vagus nerve on the intended side of the neck. It is understood, however, that the fluorescence alignment method described above may not be suitable for all patients, particularly patients having necks that are significantly wrinkled or that contain large amounts of fatty tissue.

In one embodiment of the present invention, significant portions of the control of the vagus nerve stimulation reside in controller components that are physically separate from the housing of the stimulator. In this embodiment, separate components of the controller and stimulator housing generally communicate with one another wirelessly. Thus, the use of wireless technology avoids the inconvenience and distance limitations of interconnecting cables. Additional reasons in the present disclosure for physically separating many components of the controller from the stimulator housing are as follows.

First, the stimulator may be constructed with the minimum number of components needed to generate the stimulation pulses, with the remaining components placed in parts of the controller that reside outside the stimulator housing, resulting in a lighter and smaller stimulator housing. In fact, the stimulator housing may be made so small that it could be difficult to place, on the stimulator housing's exterior, switches and knobs that are large enough to be operated easily. Instead, for the present disclosure, the user may generally operate the device using the smartphone touchscreen.

Second, the controller (330 in FIG. 1C) may be given additional functions when free from the limitation of being situated within or near the stimulator housing. For example, one may add to the controller a data logging component that records when and how stimulation has been applied to the patient, for purposes of medical recordkeeping and billing. The complete electronic medical record database for the patient may be located far from the stimulator (e.g., somewhere on the internet), and the billing system for the stimulation services that are provided may also be elsewhere, so it would be useful to integrate the controller into that recordkeeping and billing system, using a communication system that includes access to the internet or telephone networks.

Third, communication from the databases to the controller would also be useful for purposes of metering electrical stimulation of the patient, when the stimulation is self-administered. For example, if the prescription for the patient only permits only a specified amount of stimulation energy to be delivered during a single session of vagus nerve stimulation, followed by a wait-time before allowing the next stimulation, the controller can query the database and then permit the stimulation only when the prescribed wait-time has passed. Similarly, the controller can query the billing system to assure that the patient's account is in order, and withhold the stimulation if there is a problem with the account.

Fourth, as a corollary of the previous considerations, the controller may be constructed to include a computer program separate from the stimulating device, in which the databases are accessed via cell phone or internet connections.

Fifth, in some applications, it is desired that the stimulator housing and parts of the controller be physically separate. For example, when the patient is a child, one wants to make it impossible for the child to control or adjust the vagus nerve stimulation. The best arrangement in that case is for the stimulator housing to have no touchscreen elements, control switches or adjustment knobs that could be activated by the child. Alternatively, any touchscreen elements, switches and knobs on the stimulator can be disabled, and control of the stimulation then resides only in a remote controller with a child-proof operation, which would be maintained under the control of a parent or healthcare provider.

Sixth, in some applications, the particular control signal that is transmitted to the stimulator by the controller will depend on physiological and environmental signals that are themselves transmitted to and analyzed by the controller. In such applications, many of the physiological and environmental signals may already be transmitted wirelessly, in which case it is most convenient to design an external part of the controller as the hub of all such wireless activity, including any wireless signals that are sent to and from the stimulator housing.

With these considerations in mind, an embodiment of the invention includes a base station that may send/receive data to/from the stimulator, and may send/receive data to/from databases and other components of the system, including those that are accessible via the internet. Typically, the base station will be a laptop computer attached to additional components needed for it to accomplish its function. Thus, prior to any particular stimulation session, the base station may load into the stimulator (FIG. 3) parameters of the session, including waveform parameters, or the actual waveform. See FIG. 2. In one embodiment, the base station is also used to limit the amount of stimulation energy that may be consumed by the patient during the session, by charging the stimulator's rechargable battery (see 41 in FIG. 3) with only a specified amount of releasable electrical energy, which is different than setting a parameter to restrict the duration of a stimulation session. Thus, the base station may comprise a power supply that may be connected to the stimulator's rechargable battery, and the base station meters the recharge. As a practical matter, the stimulator may therefore use two batteries, one for applying stimulation energy to the electrodes (the charge of which may be limited by the base station) and the other for performing other functions. Methods for evaluating a battery's charge or releasable energy are known in the art, for example, in patent U.S. Pat. No. 7,751,891, entitled Power supply monitoring for an implantable device, to ARMSTRONG et al. Alternatively, control components within the stimulator housing may monitor the amount of electrode stimulation energy that has been consumed during a stimulation session and stop the stimulation session when a limit has been reached, irrespective of the time when the limit has been reached.

Figure 7:
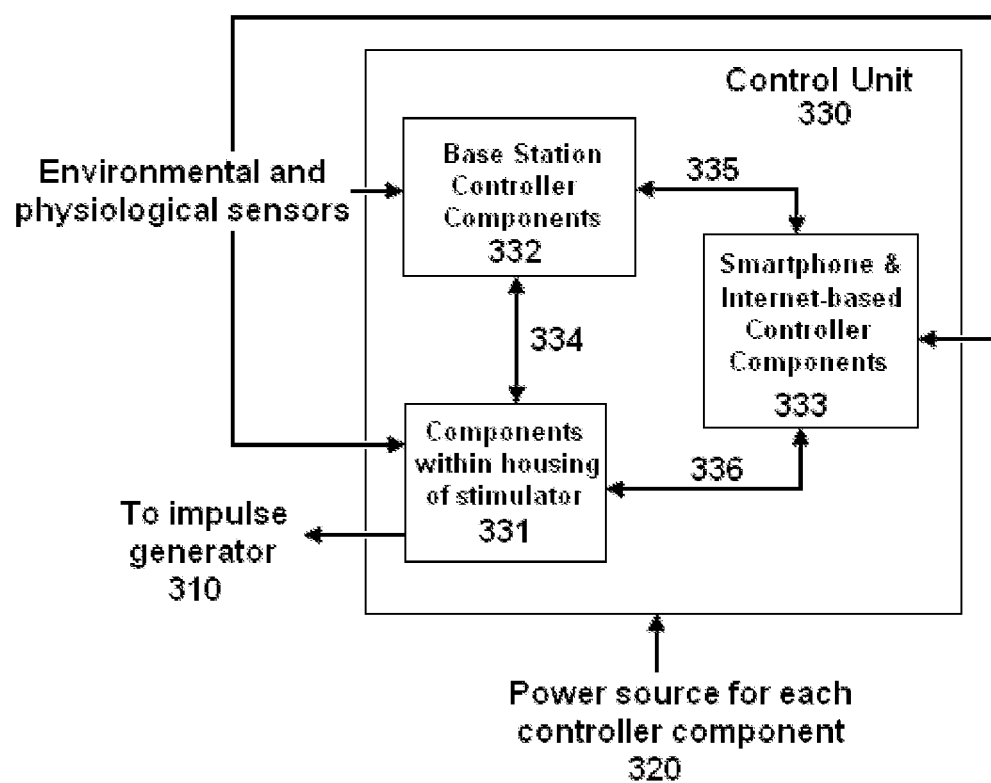
FIG. 7 shows an expanded diagram of the control unit shown in FIG. 1, separating components of the control unit into those within the housing of the stimulator, those within a base station, and those within smartphone and internet-based devices, also showing communication paths between such components.

The communication connections between different components of the stimulator's controller are shown in FIG. 7, which is an expanded representation of the control unit 330 in FIG. 1C. Connection between the base station controller components 332 and components within the stimulator housing 331 is denoted in FIG. 7 as 334. Connection between the base station controller components 332 and internet-based or smartphone components 333 is denoted as 335. Connection between the components within the stimulator housing 331 and internet-based or smartphone components 333 is denoted as 336. For example, control connections between the smartphone and stimulator housing via the audio jack socket would fall under this category, as would any wireless communication directly between the stimulator housing itself and a device situated on the internet. In principle, the connections 334, 335 and 336 in FIG. 7 may be either wired or wireless. Different embodiments of the invention may lack one or more of the connections.

Although infrared or ultrasound wireless control might be used to communicate between components of the controller, they are not preferred because of line-of-sight limitations. Instead, in the present disclosure, the communication between devices preferably makes use of radio communication within unlicensed ISM frequency bands (260-470 MHz, 902-928 MHz, 2400-2.4835 GHz). Components of the radio frequency system in devices in 331, 332, and 333 typically comprise a system-on-chip transciever with an integrated microcontroller; a crystal; associated balun & matching circuitry, and an antenna [Dag GRINI. RF Basics, RF for Non-RF Engineers. Texas Instruments, Post Office Box 655303, Dallas, Tex. 75265, 2006].

Transceivers based on 2.4 GHz offer high data rates (greater than 1 Mbps) and a smaller antenna than those operating at lower frequencies, which makes them suitable for with short-range devices. Furthermore, a 2.4 GHz wireless standard (Bluetooth, Wi-Fi, and ZigBee) may be used as the protocol for transmission between devices. Although the ZigBee wireless standard operates at 2.4 GHz in most jurisdictions worldwide, it also operates in the ISM frequencies 868 MHz in Europe, and 915 MHz in the USA and Australia. Data transmission rates vary from 20 to 250 kilobits/second with that standard. Because many commercially available health-related sensors may operate using ZigBee, its use may be recommended for applications in which the controller uses feedback and feedforward methods to adjust the patient's vagus nerve stimulation based on the sensors' values, as described below in connection with FIG. 11 [ZigBee Wireless Sensor Applications for Health, Wellness and Fitness. ZigBee Alliance 2400 Camino Ramon Suite 375 San Ramon, Calif. 94583].

A 2.4 GHz radio has higher power consumption than radios operating at lower frequencies, due to reduced circuit efficiencies. Furthermore, the 2.4 GHz spectrum is crowded and subject to significant interference from microwave ovens, cordless phones, 802.11b/g wireless local area networks, Bluetooth devices, etc. Sub-GHz radios enable lower power consumption and can operate for years on a single battery. These factors, combined with lower system cost, make sub-GHz transceivers ideal for low data rate applications that need maximum range and multi-year operating life.

The antenna length needed for operating at different frequencies is 17.3 cm at 433 MHz, 8.2 cm at 915 MHz, and 3 cm at 2.4 GHz. Therefore, unless the antenna is included in a neck collar that supports the device shown in FIG. 3, the antenna length may be a disadvantage for 433 MHz transmission. The 2.4 GHz band has the advantage of enabling one device to serve in all major markets worldwide since the 2.4 GHz band is a global spectrum standard. However, 433 MHz is a viable alternative to 2.4 GHz for most of the world, and designs based on 868 and 915 MHz radios can serve the US and European markets with a single product.

Range is determined by the sensitivity of the transceiver and its output power. A primary factor affecting radio sensitivity is the data rate. Higher data rates reduce sensitivity, leading to a need for higher output power to achieve sufficient range. For many applications that require only a low data rate, the preferred rate is 40 Kbps where the transceiver can still use a standard off-the-shelf 20 parts per million crystal.

A typical signal waveform that might be transmitted wirelessly to the stimulator housing was shown in FIGS. 2B and 2C. As seen there, individual sinusoidal pulses have a period of tau, and a burst consists of N such pulses. This is followed by a period with no signal (the inter-burst period). The pattern of a burst followed by silent inter-burst period repeats itself with a period of T. For example, the sinusoidal period tau may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 2C to make the bursts discernable). When these exemplary values are used for T and tau, the waveform contains significant Fourier components at higher frequencies (1/200 microseconds=5000/sec). Such a signal may be easily transmitted using 40 Kbps radio transmission. Compression of the signal is also possible, by transmitting only the signal parameters tau, N, T, Emax, etc., but in that case the stimulator housing's control electronics would then have to construct the waveform from the transmitted parameters, which would add to the complexity of components of the stimulator housing.

However, because it is contemplated that sensors attached to the stimulator housing may also be transmitting information, the data transfer requirements may be substantially greater than what is required only to transmit the signal shown in FIG. 2. Therefore, the present invention may make use of any frequency band, not limited to the ISM frequency bands, as well as techniques known in the art to suppress or avoid noise and interferences in radio transmission, such as frequency hopping and direct sequence spread spectrum.

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retropharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

FIG. 8 illustrates use of the device 30 shown in FIG. 3 (30 in FIG. 8=31+32 in FIG. 3) to stimulate the vagus nerve at that location in the neck, in which the stimulator device 30 is shown to be applied to the target location on the patient's neck as described above. For reference, FIG. 8 shows the locations of the following vertebrae: first cervical vertebra 71, the fifth cervical vertebra 75, the sixth cervical vertebra 76, and the seventh cervical vertebra 77. Because the smartphone is applied to the patient's neck, the patient will generally need a mirror 29 to view and touch the phone's touchscreen. Therefore, the images displayed on the phone's screen may be reversed when the device is used as shown in FIG. 8. Alternatively, the images displayed on the phone's screen may be transmitted wirelessly to a computer program in the base station, which will display the images on the computer screen of the base station, and the patient may interact with the smartphone wirelessly via the base station.

Figure 9:
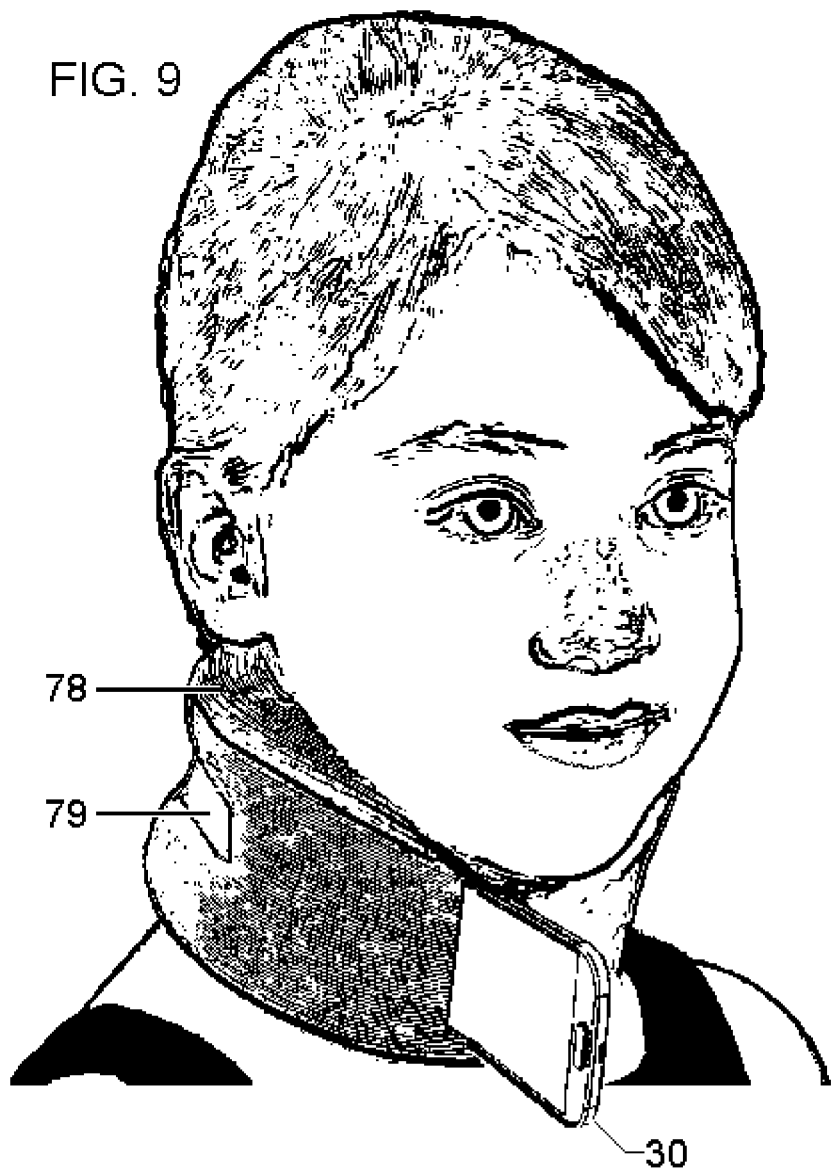
FIG. 9 illustrates the approximate position of the stimulator according one embodiment of the present invention, when used to stimulate the right vagus nerve in the neck of a child who wears a collar to hold the stimulator.

FIG. 9 shows the stimulator 30 applied to the neck of a child, which is partially immobilized with a foam cervical collar 78 that is similar to ones used for neck injuries and neck pain. The collar is tightened with a strap 79, and the stimulator is inserted through a hole in the collar to reach the child's neck surface. In such applications, the stimulator may be turned on and off remotely, using a wireless controller that may be used to adjust the stimulation parameters of the controller (e.g., on/off, stimulation amplitude, frequency, etc.).

FIG. 10 provides a more detailed view of use of the electrical stimulator 30, when positioned to stimulate the vagus nerve at the neck location that is indicated in FIG. 8. The anatomy shown in FIG. 10 is a cross-section of half of the neck at vertebra level C6. The vagus nerve 60 is identified in FIG. 10, along with the carotid sheath 61 that is identified there in bold peripheral outline. The carotid sheath encloses not only the vagus nerve, but also the internal jugular vein 62 and the common carotid artery 63. Structures that may be identified near the surface of the neck include the external jugular vein 64 and the sternocleidomastoid muscle 65, which protrudes when the patient turns his or her head. Additional organs in the vicinity of the vagus nerve include the trachea 66, thyroid gland 67, esophagus 68, scalenus anterior muscle 69, scalenus medius muscle 70, levator scapulae muscle 71, splenius colli muscle 72, semispinalis capitis muscle 73, semispinalis colli muscle 74, longus colli muscle and longus capitis muscle 75. The sixth cervical vertebra 76 is shown with bony structure indicated by hatching marks. Additional structures shown in the figure are the phrenic nerve 77, sympathetic ganglion 78, brachial plexus 79, vertebral artery and vein 80, prevertebral fascia 81, platysma muscle 82, omohyoid muscle 83, anterior jugular vein 84, sternohyoid muscle 85, sternothyroid muscle 86, and skin with associated fat 87.

Methods of treating a patient comprise stimulating the vagus nerve as indicated in FIGS. 8, 9, and 10, using the electrical stimulation devices that are disclosed here. Stimulation may be performed on the left or right vagus nerve or on both of them simultaneously or alternately. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, harnesses, or frames may be used to maintain the stimulator in position. The stimulator signal may have a frequency and other parameters that are selected to produce a therapeutic result in the patient, i.e., stimulation parameters for each patient are adjusted on an individualized basis. Ordinarily, the amplitude of the stimulation signal is set to the maximum that is comfortable for the patient, and then the other stimulation parameters are adjusted.

The stimulation is then performed with a sinusoidal burst waveform like that shown in FIG. 2. As seen there, individual sinusoidal pulses have a period of $\tau$, and a burst consists of N such pulses. This is followed by a period with no signal (the inter-burst period). The pattern of a burst followed by silent inter-burst period repeats itself with a period of T. For example, the sinusoidal period $\tau$ may be between about 50-1000 microseconds (equivalent to about 1-20 KHz), preferably between about 100-400 microseconds (equivalent to about 2.5-10 KHz), more preferably about 133-400 microseconds (equivalent to about 2.5-7.5 KHZ) and even more preferably about 200 microseconds (equivalent to about 5 KHz); the number of pulses per burst may be N=1-20, preferably about 2-10 and more preferably about 5; and the whole pattern of burst followed by silent inter-burst period may have a period T comparable to about 10-100 Hz, preferably about 15-50 Hz, more preferably about 25-35 Hz and even more preferably about 25 Hz (a much smaller value of T is shown in FIG. 2C to make the bursts discernable). When these exemplary values are used for T and $\tau$, the waveform contains significant Fourier components at higher frequencies (1/200 microseconds=5000/sec), as compared with those contained in transcutaneous nerve stimulation waveforms, as currently practiced.

When a patient is using the stimulation device to perform self-stimulation therapy, e.g., at home or at a workplace, he or she will follow the steps that are now described. It is assumed that the optimal stimulation position has already been marked on the patient's neck, as described above and that a reference image of the fluorescent spots has already been acquired. The previous stimulation session will ordinarily have discharged the rechargeable batteries of the stimulator housing, and between sessions, the base station will have been used to recharged the stimulator at most only up to a minimum level. If the stimulator's batteries had charge remaining from the previous stimulation session, the base station will discharge the stimulator to a minimum level that will not support stimulation of the patient.

The patient can initiate the stimulation session using the mobile phone or base station (e.g., laptop computer) by invoking a computer program (on the laptop computer or through an app on the mobile phone) that is designed to initiate use of the stimulator. The programs in the smartphone and base station may initiate and interact with one another wirelessly, so in what follows, reference to the program (app) in the smartphone may also apply to the program in the base station, because both may be operating in tandem. For security reasons, the program would begin with the request for a user name and a password, and that user's demographic information and any data from previous stimulator experiences would already be associated with it in the login account. The smartphone may also be used to authenticate the patient using a fingerprint or voice recognition app, or other reliable authentication methods. If the patient's physician has not authorized further treatments, the base station will not charge the stimulator's batteries, and instead, the computer program will call or otherwise communicate with the physician's computer requesting authorization. After authorization by the physician is received, the computer program (on the laptop computer or through an app on the mobile phone) may also query a database that is ordinarily located somewhere on the internet to verify that the patient's account is in order. If it is not in order, the program may then request prepayment for one or more stimulation sessions, which would be paid by the patient using a credit card, debit card, PayPal or the like. The computer program will also query its internal database or that of the base station to determine that sufficient time has elapsed between when the stimulator was last used and the present time, to verify that any required wait-time has elapsed.

Having received authorization to perform a nerve stimulation session, the patient interface computer program will then ask the patient questions that are relevant to the selection of parameters that the base station will use to make the stimulator ready for the stimulation session. The questions that the computer program asks are dependent on the condition for which the patient is being treated, which for present purposes is considered to be treatment for a migraine headache. That headache may in principle be in any of the headache phases (prodrome, aura, headache pain, postdrome, and interictal period), which would be ascertained through the computer program's questions. The questions may be things like (1) is this an acute or prophylactic treatment? (2) if acute, then how severe is your headache, how long have you had it, (3) has anything unusual or noteworthy occurred since the last stimulation?, etc. In general, the types of posed questions are ones that would be placed in a headache diary [TASSORELLI C, Sances G, Allena M, Ghiotto N, Bendtsen L, Olesen J, Nappi G, Jensen R. The usefulness and applicability of a basic headache diary before first consultation: results of a pilot study conducted in two centers. Cephalalgia 28(10, 2008):1023-1030].

Having received such preliminary information from the patient, the computer programs will perform instrument diagnostic tests and make the stimulator ready for the stimulation session. In general, the algorithm for setting the stimulator parameters will have been decided by the physician and will include the extent to which the stimulator batteries should be charged, which the vagus nerve should be stimulated (right or left), and the time that the patient should wait after the stimulation session is ended until initiation of a subsequent stimulation session. The computer will query the physician's computer to ascertain whether there have been any updates to the algorithm, and if not, will use the existing algorithm. The patient will also be advised of the stimulation session parameter values by the interface computer program, so as to know what to expect.

Once the base station has been used to charge the stimulator's batteries to the requisite charge, the computer program (or smartphone app) will indicate to the patient that the stimulator is ready for use. At that point, the patient would attach to the smartphone the optical attachment 50 shown in FIG. 5, clean the electrode surfaces, and make any other preliminary adjustments to the hardware. The stimulation parameters for the session will be displayed, and any options that the patient is allowed to select may be made. Once the patient is ready to begin, he or she will press a "start" button on the touchscreen and may begin the vagus nerve stimulation, as shown in FIG. 8.

Multiple methods may be used to test whether the patient is properly attempting to stimulate the vagus nerve on the intended side of the neck. For example, accelerometers and gyroscopes within the smartphone may be used to determine the position and orientation of the smartphone's touch screen relative to the patient's expected view of the screen, and a decision by the stimulator's computer program as to which hand is being used to hold the stimulator may be made by measuring capacitance on the outside of the stimulator body, which may distinguish fingers wrapped around the device versus the ball of a thumb [Raphael WIMMER and Sebastian Boring. HandSense: discriminating different ways of grasping and holding a tangible user interface. Proceedings of the 3rd International Conference on Tangible and Embedded Interaction, pp. 359-362. ACM New York, N.Y., 2009]. Pressing of the electrodes against the skin will result in a resistance drop across the electrodes, which can initiate operation of the rear camera. A fluorescent image should appear on the smartphone screen only if the device is applied to the side of the neck in the vicinity of the fluorescent spots that had been applied as a tattoo earlier. If the totality of these data indicates to the computer program that the patient is attempting to stimulate the wrong vagus nerve or that the device is being held improperly, the stimulation will be withheld, and the stimulator may then communicate with the patient via the interface computer program (in the mobile phone or laptop computer) to alert the patient of that fact. The program may then offer suggestions on how to better apply the device to the neck.

However, if the stimulator is being properly applied, and an image of the fluorescent spots on the patient's neck appears on the screen of the phone, the stimulator begins to stimulate according to predetermined initial stimulus parameters. The patient will then adjust the position and angular orientation of the stimulator about what he or she thinks is the correct neck position, until he or she perceives stimulation when current is passed through the stimulator electrodes. An attempt is also made to superimpose the currently viewed fluorescence image of the neck spots with the previously acquired reference image. The applied current is increased gradually using keys on the keyboard of the base station or on the smartphone touchscreen, first to a level wherein the patient feels sensation from the stimulation. The stimulation amplitude is then increased by the patient, but is set to a level that is less than one at which he first senses any discomfort. By trial and error, the stimulation is then optimized by the patient, who tries to find the greatest acceptable sensation with the lowest acceptable stimulation amplitude, with the stimulator aligned using the fluorescent spots. If the stimulator is being held in place by hand, it is likely that there may be inadvertent fluctuating movement of the stimulator, due for example to neck movement during respiration. Such relative movements will affect the effectiveness of the stimulation. However, they may be monitored by accelerometers and gyroscopes within the smartphone, which may be transmitted as movement data from the stimulator to the patient interface computer program (in the mobile phone or laptop computer). The relative movements may also be monitored and measured as fluctuations in the position of the fluorescence spots that are being imaged. By watching a graphical display of the relative movements shown by the patient interface computer program, the patient may use that display in an attempt to deliberately minimize the movements. Otherwise, the patient may attempt to adjust the amplitude of the stimulator as compensation for movement of the stimulator away from its optimum position. In a section that follows, it is described how the stimulator itself may modulate the amplitude of the stimulation in order to make such compensations.

During the session, the patient may lift the stimulator from his neck, which will be detected as an increase in resistance between the electrodes and a loss of the fluorescent image of the spots on the patient's neck. When that occurs, the device will withhold power to the stimulator for reasons of safety. The patient can then reapply the stimulator to his neck to resume the session, although the interruption of stimulation will be recognized and recorded by the computer program. Stimulation by the patient will then continue until the battery of the stimulator is depleted, or the patient decides to terminate the stimulation session. At that point, the patient will acknowledge that the stimulation session is finished by touching a response button on the smartphone screen, whereupon the stimulator will transfer to the base station data that its microprocessor has caused to be stored regarding the stimulation session (e.g., stimulation amplitude as a function of time and information about movements of the device during the session, duration of the stimulation, the existence of interruptions, etc.). Such information will then be transmitted to and displayed by the patient interface computer program (in the mobile phone or laptop computer), which will subsequently ask the patient questions regarding the effectiveness of the stimulation. Such questions may be in regards to the post-stimulation severity of the headache, whether the severity decreased gradually or abruptly during the course of the stimulation, and whether anything unusual or noteworthy occurred during the stimulation. All such post-stimulation data will also be delivered over the internet by the patient interface computer program to the physician's computer for review and possible adjustment of the algorithm that is used to select stimulation parameters and regimens. It is understood that the physician will adjust the algorithm based not only on the experience of each individual patient, but on the experience of all patients collectively so as to improve effectiveness of the stimulator's use, for example, by identifying characteristics of most and least responsive patients.

Before logging off of the interface computer program, the patient may also review database records and summaries about all previous treatment sessions, so as to make his or her own judgment about treatment progress. If the stimulation was part of a prophylactic treatment regimen that was prescribed by the patient's physician, the patient interface computer program will remind the patient about the schedule for the upcoming self-treatment sessions and allow for a rescheduling if necessary.

For some patients, the stimulation may be performed for as little as 90 seconds, but it may also be for up to 30 minutes or longer. The treatment is generally performed once or twice daily or several times a week, for 12 weeks or longer before a decision is made as to whether to continue the treatment. For patients experiencing intermittent symptoms, the treatment may be performed only when the patient is symptomatic. However, it is understood that parameters of the stimulation protocol may be varied in response to heterogeneity in the pathophysiology of patients. Different stimulation parameters may also be used as the course of the patient's condition changes.

In some embodiments of the invention, pairing of vagus nerve stimulation may be with a additional sensory stimulation. The paired sensory stimulation may be bright light, sound, tactile stimulation, or electrical stimulation of the tongue to simulate odor/taste, e.g., pulsating with the same frequency as the vagus nerve electrical stimulation. The rationale for paired sensory stimulation is the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect. This pairing may be considered especially when some such corresponding sensory circuit of the brain is thought to be partly responsible for triggering the migraine headache.

Selection of stimulation parameters to preferentially stimulate particular regions of the brain may be done empirically, wherein a set of stimulation parameters are chosen, and the responsive region of the brain is measured using fMRI or a related imaging method [CHAE JH, Nahas Z, Lomarev M, Denslow S, Lorberbaum J P, Bohning D E, George M S. A review of functional neuroimaging studies of vagus nerve stimulation (VNS). J Psychiatr Res. 37(6, 2003):443-455; CONWAY CR, Sheline Y I, Chibnall J T, George M S, Fletcher J W, Mintun M A. Cerebral blood flow changes during vagus nerve stimulation for depression. Psychiatry Res. 146(2, 2006):179-84]. Thus, by performing the imaging with different sets of stimulation parameters, a database may be constructed, such that the inverse problem of selecting parameters to match a particular brain region may be solved by consulting the database.

The individualized selection of parameters for the nerve stimulation protocol may based on trial and error in order to obtain a beneficial response without the sensation of skin pain or muscle twitches. Alternatively, the selection of parameter values may involve tuning as understood in control theory, as described below. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10(5, 2004):378-82].

The vagus nerve stimulation may employ methods of control theory (e.g., feedback) in an attempt to compensate for motion of the stimulator relative to the vagus nerve and to avoid potentially dangerous situations such as excessive heart rate. Thus, with these methods, the parameters of the vagus nerve stimulation may be changed automatically, depending on environmental signals or on physiological measurements that are made, in attempt to maintain the values of the physiological signals within predetermined ranges.

When stimulating the vagus nerve, motion variability may often be attributable to the patient's breathing, which involves contraction and associated change in geometry of the sternocleidomastoid muscle that is situated close to the vagus nerve (identified as 65 in FIG. 10). Modulation of the stimulator amplitude to compensate for this variability may be accomplished by measuring the patient's respiratory phase, or more directly by measuring movement of the stimulator, then using controllers (e.g., PID controllers) that are known in the art of control theory, as now described.

FIG. 11 is a control theory representation of the disclosed vagus nerve stimulation methods. The "System" (patient) receives input from the "Environment." For example, the environment would include ambient temperature, light, and sound, all of which may be triggers of a migraine attack. If the "System" is defined to be only a particular physiological component of the patient, the "Environment" may also be considered to include physiological systems of the patient that are not included in the "System". Thus, if some physiological component can influence the behavior of another physiological component of the patient, but not vice versa, the former component could be part of the environment and the latter could be part of the system. On the other hand, if it is intended to control the former component to influence the latter component, then both components should be considered part of the "System."

The system also receives input from the "Controller", which in this case may comprise the vagus nerve stimulation device, as well as electronic components that may be used to select or set parameters for the stimulation protocol (amplitude, frequency, pulse width, burst number, etc.) or alert the patient as to the need to use or adjust the stimulator (i.e., an alarm). For example, the controller may comprise the control unit 330 in FIG. 1C. Feedback in the schema shown in FIG. 11 is possible because physiological measurements of the System are made using sensors. Thus, the values of variables of the system that could be measured define the system's state ("the System Output"). As a practical matter, only some of those measurements are actually made, and they represent the "Sensed Physiological Input" to the Controller.

The preferred sensors will include ones ordinarily used for ambulatory monitoring. For example, the sensors may comprise those used in conventional Holter and bedside monitoring applications, for monitoring heart rate and variability, ECG, respiration depth and rate, core temperature, hydration, blood pressure, brain function, oxygenation, skin impedance, and skin temperature. The sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. The ECG sensors should be adapted to the automatic extraction and analysis of particular features of the ECG, for example, indices of P-wave morphology, as well as heart rate variability indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. An event marker may also be included in order for the patient to mark relevant circumstances and sensations.

For brain monitoring, the sensors may comprise ambulatory EEG sensors [CASSON A, Yates D, Smith S, Duncan J, Rodriguez-Villegas E. Wearable electroencephalography. What is it, why is it needed, and what does it entail? IEEE Eng Med Biol Mag. 29(3, 2010):44-56] or optical topography systems for mapping prefrontal cortex activation [Atsumori H, Kiguchi M, Obata A, Sato H, Katura T, Funane T, Maki A. Development of wearable optical topography system for mapping the prefrontal cortex activation. Rev Sci Instrum. 2009 April; 80(4):043704]. Signal processing methods, comprising not only the application of conventional linear filters to the raw EEG data, but also the nearly real-time extraction of non-linear signal features from the data, may be considered to be a part of the EEG monitoring [D. Puthankattil SUBHA, Paul K. Joseph, Rajendra Acharya U, and Choo Min Lim. EEG signal analysis: A survey. J Med Syst 34(2010):195-212]. Such features would include EEG bands (e.g., delta, theta, alpha, beta).

Detection of the phase of respiration may be performed non-invasively by adhering a thermistor or thermocouple probe to the patient's cheek so as to position the probe at the nasal orifice. Strain gauge signals from belts strapped around the chest, as well as inductive plethysmography and impedance pneumography, are also used traditionally to non-invasively generate a signal that rises and falls as a function of the phase of respiration. Respiratory phase may also be inferred from movement of the sternocleidomastoid muscle that also causes movement of the vagus nerve stimulator during breathing, measured using accelerometers attached to the vagus nerve stimulator, as described below. After digitizing such signals, the phase of respiration may be determined using software such as "puka", which is part of PhysioToolkit, a large published library of open source software and user manuals that are used to process and display a wide range of physiological signals [GOLDBERGER A L, Amaral L A N, Glass L, Hausdorff J M, Ivanov P Ch, Mark R G, Mietus J E, Moody G B, Peng C K, Stanley H E. PhysioBank, PhysioToolkit, and PhysioNet: Components of a New Research Resource for Complex Physiologic Signals. Circulation 101(23, 2000):e215-e220] available from PhysioNet, M.I.T. Room E25-505A, 77 Massachusetts Avenue, Cambridge, Mass. 02139]. In one embodiment of the present invention, the control unit 330 contains an analog-to-digital converter to receive such analog respiratory signals, and software for the analysis of the digitized respiratory waveform resides within the control unit 330. That software extracts turning points within the respiratory waveform, such as end-expiration and end-inspiration, and forecasts future turning points, based upon the frequency with which waveforms from previous breaths match a partial waveform for the current breath. The control unit 330 then controls the impulse generator 310, for example, to stimulate the selected nerve only during a selected phase of respiration, such as all of inspiration or only the first second of inspiration, or only the expected middle half of inspiration. In other embodiments of the invention, the physiological or environmental signals are transmitted wirelessly to the controller, as shown in FIG. 7. Some such signals may be received by the base station (e.g., ambient sound signals) and other may be received within the stimulator housing (e.g., motion signals).

It may be therapeutically advantageous to program the control unit 330 to control the impulse generator 310 in such a way as to temporally modulate stimulation by the electrodes, depending on the phase of the patient's respiration. In patent application JP2008/081479A, entitled Vagus nerve stimulation system, to YOSHIHOTO, a system is also described for keeping the heart rate within safe limits. When the heart rate is too high, that system stimulates a patient's vagus nerve, and when the heart rate is too low, that system tries to achieve stabilization of the heart rate by stimulating the heart itself, rather than use different parameters to stimulate the vagus nerve. In that disclosure, vagal stimulation uses an electrode, which is described as either a surface electrode applied to the body surface or an electrode introduced to the vicinity of the vagus nerve via a hypodermic needle. That disclosure is unrelated to the headache problems that are addressed here, but it does consider stimulation during particular phases of the respiratory cycle, for the following reason. Because the vagus nerve is near the phrenic nerve, Yoshihoto indicates that the phrenic nerve will sometimes be electrically stimulated along with the vagus nerve. The present applicants have not experienced this problem, so the problem may be one of a misplaced electrode. In any case, the phrenic nerve controls muscular movement of the diaphragm, so consequently, stimulation of the phrenic nerve causes the patient to hiccup or experience irregular movement of the diaphragm, or otherwise experience discomfort. To minimize the effects of irregular diaphragm movement, Yoshihoto's system is designed to stimulate the phrenic nerve (and possibly co-stimulate the vagus nerve) only during the inspiration phase of the respiratory cycle and not during expiration. Furthermore, the system is designed to gradually increase and then decrease the magnitude of the electrical stimulation during inspiration (notably amplitude and stimulus rate) so as to make stimulation of the phrenic nerve and diaphragm gradual.

Furthermore, as an option in the present invention, parameters of the stimulation may be modulated by the control unit 330 to control the impulse generator 310 in such a way as to temporally modulate stimulation by the electrodes, so as to achieve and maintain the heart rate within safe or desired limits. In that case, the parameters of the stimulation are individually raised or lowered in increments (power, frequency, etc.), and the effect as an increased, unchanged, or decreased heart rate is stored in the memory of the control unit 330. When the heart rate changes to a value outside the specified range, the control unit 330 automatically resets the parameters to values that had been recorded to produce a heart rate within that range, or if no heart rate within that range has yet been achieved, it increases or decreases parameter values in the direction that previously acquired data indicate would change the heart rate in the direction towards a heart rate in the desired range. Similarly, the arterial blood pressure is also recorded non-invasively in an embodiment of the invention, and as described above, the control unit 330 extracts the systolic, diastolic, and mean arterial blood pressure from the blood pressure waveform. The control unit 330 will then control the impulse generator 310 in such a way as to temporally modulate nerve stimulation by the electrodes, in such a way as to achieve and maintain the blood pressure within predetermined safe or desired limits, by the same method that was indicated above for the heart rate.

Let the measured output variables of the system in FIG. 11 be denoted by $y_i$ (i=1 to Q); let the desired (reference or setpoint) values of $y_i$ be denoted by $r_i$ and let the controller's input to the system consist of variables $u_j$ (j=1 to P). The objective is for a controller to select the input $u_j$ in such a way that the output variables (or a subset of them) closely follows the reference signals $r_i$, i.e., the control error $e_i=r_i-y_i$ is small, even if there is environmental input or noise to the system. Consider the error function $e_i=r_i-y_i$ to be the sensed physiological input to the controller in FIG. 11 (i.e., the reference signals are integral to the controller, which subtracts the measured system values from them to construct the control error signal). The controller will also receive a set of measured environmental signals $v_k$ (k=1 to R), which also act upon the system as shown in FIG. 11.

The functional form of the system's input u(t) is constrained to be as shown in FIGS. 2B and 2C. Ordinarily, a parameter that needs adjusting is the one associated with the amplitude of the signal shown in FIG. 2. As a first example of the use of feedback to control the system, consider the problem of adjusting the input u(t) from the vagus nerve stimulator (i.e., output from the controller) in order to compensate for motion artifacts.

Nerve activation is generally a function of the second spatial derivative of the extracellular potential along the nerve's axon, which would be changing as the position of the stimulator varies relative to the axon [F. RATTAY. The basic mechanism for the electrical stimulation of the nervous system. Neuroscience 89 (2, 1999):335-346]. Such motion artifact can be due to movement by the patient (e.g., neck movement) or movement within the patient (e.g. sternocleidomastoid muscle contraction associated with respiration), or it can be due to movement of the stimulator relative to the body (slippage or drift). Thus, one expects that because of such undesired or unavoidable motion, there will usually be some error (e=r−y) in the intended (r) versus actual (y) nerve stimulation amplitude that needs continuous adjustment.

Accelerometers can be used to detect all these types of movement, using for example, Model LSM330DL from STMicroelectronics, 750 Canyon Dr #300 Coppell, Tex. 75019. In one embodiment, one or more accelerometer is attached to the patient's neck, and one or more accelerometer is attached to the head(s) of the stimulator in the vicinity of where the stimulator contacts the patient, or an accelerometer within the smartphone is used. Because the temporally integrated outputs of the accelerometers provide a measurement of the current position of each accelerometer, the combined accelerometer outputs make it possible to measure any movement of the stimulator relative to the underlying tissue.

The location of the vagus nerve underlying the stimulator may be determined preliminarily by placing an ultrasound probe at the location where the center of the stimulator will be placed [KNAPPERTZ VA, Tegeler C H, Hardin S J, McKinney W M. Vagus nerve imaging with ultrasound: anatomic and in vivo validation. Otolaryngol Head Neck Surg 118(1, 1998):82-5]. The ultrasound probe is configured to have the same shape as the stimulator, including the attachment of one or more accelerometer. As part of the preliminary protocol, the patient with accelerometers attached is then instructed or helped to perform neck movements, breathe deeply so as to contract the sternocleidomastoid muscle, and generally simulate possible motion that may accompany prolonged stimulation with the stimulator. This would include possible slippage or movement of the stimulator relative to an initial position on the patient's neck. While these movements are being performed, the accelerometers are acquiring position information, and the corresponding location of the vagus nerve is determined from the ultrasound image. With these preliminary data, it is then possible to infer the location of the vagus nerve relative to the stimulator, given only the accelerometer data during a stimulation session, by interpolating between the previously acquired vagus nerve position data as a function of accelerometer position data. Such data would complement imaging data that measure the extent to which the current fluorescence images of the spots on the patient's neck coincide with a reference image, and therefore also measure the relative movement of the stimulator.

For any given position of the stimulator relative to the vagus nerve, it is also possible to infer the amplitude of the electric field that it produces in the vicinity of the vagus nerve. This is done by calculation or by measuring the electric field that is produced by the stimulator as a function of depth and position within a phantom that simulates the relevant bodily tissue [Francis Marion MOORE. Electrical Stimulation for pain suppression: mathematical and physical models. Thesis, School of Engineering, Cornell University, 2007; Bartosz SAWICKI, Robert Szmurto, Przemystaw Ptonecki, Jacek Starzynski, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Thus, in order to compensate for movement, the controller may increase or decrease the amplitude of the output from the stimulator (u) in proportion to the inferred deviation of the amplitude of the electric field in the vicinity of the vagus nerve, relative to its desired value.

For present purposes, no distinction is made between a system output variable and a variable representing the state of the system. Then, a state-space representation, or model, of the system consists of a set of first order differential equations of the form $dy_i/dt=F_i(t,\{y_i\},\{u_j\},\{v_k\};\{r_i\})$, where t is time and where in general, the rate of change of each variable $y_i$ is a function ($F_i$) of many other output variables as well as the input and environmental signals.

Classical control theory is concerned with situations in which the functional form of $F_i$ is as a linear combination of the state and input variables, but in which coefficients of the linear terms are not necessarily known in advance. In this linear case, the differential equations may be solved with linear transform (e.g., Laplace transform) methods, which convert the differential equations into algebraic equations for straightforward solution. Thus, for example, a single-input single-output system (dropping the subscripts on variables) may have input from a controller of the form:

$$u(t) = K_p e(t) + K_i \int_0^t e(\tau)d\tau + K_d \frac{de}{dt}$$

where the parameters for the controller are the proportional gain ($K_p$), the integral gain ($K_i$) and the derivative gain ($K_d$). This type of controller, which forms a controlling input signal with feedback using the error e=r-y, is known as a PID controller (proportional-integral-derivative). Commercial versions of PID controllers are available, and they are used in 90% of all control applications.

Optimal selection of the parameters of the controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be selected according to rules that were described initially by Ziegler and Nichols. There are also many improved versions of tuning rules, including some that can be implemented automatically by the controller [L I, Y., Ang, K. H. and Chong, G. C. Y. Patents, software and hardware for PID control: an overview and analysis of the current art. IEEE Control Systems Magazine, 26 (1,2006): 42-54; Karl Johan Åström & Richard M. Murray.Feedback Systems: An Introduction for Scientists and Engineers. Princeton N.J.:Princeton University Press, 2008; Finn HAUGEN. Tuning of PID controllers (Chapter 10) In: Basic Dynamics and Control. 2009. ISBN 978-82-91748-13-9. TechTeach, Enggravhøgda 45, N-3711 Skien, Norway. http://techteach.no., pp. 129-155; Dingyu XUE, YangQuan Chen, Derek P. Atherton. PID controller design (Chapter 6), In: Linear Feedback Control: Analysis and Design with MATLAB. Society for Industrial and Applied Mathematics (SIAM). 3600 Market Street, 6th Floor, Philadelphia, Pa. (2007), pp. 183-235; Jan JANTZEN, Tuning Of Fuzzy PID Controllers, Technical University of Denmark, report 98-H 871, Sep. 30, 1998].

The controller shown in FIG. 11 may also make use of feed-forward methods [Coleman BROSILOW, Babu Joseph. Feedforward Control (Chapter 9) In: Techniques of Model-Based Control. Upper Saddle River, N.J.: Prentice Hall PTR, 2002. pp, 221-240]. Thus, the controller in FIG. 9 may be a type of predictive controller, methods for which have been developed in other contexts as well, such as when a model of the system is used to calculate future outputs of the system, with the objective of choosing among possible inputs so as to optimize a criterion that is based on future values of the system's output variables.

A disclosure of the use of such feedback and feed forward methods to forecast and avert the onset of an imminent migraine attack was made in the co-pending, commonly assigned application U.S. Ser. No. 13/357,010 (publication US 2012/0185020), entitled Nerve stimulation methods for averting imminent onset or episode of a disease, to SIMON et al, which is incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for treating a patient with seizures, the method comprising:
generating an electrical stimulation signal via a signal generator coupled to an energy source, wherein the electrical stimulation signal has a frequency of about 1 Hz to about 100 Hz;
wirelessly transmitting the electrical stimulation signal to a mobile phone remote from the signal generator;
contacting an outer surface of a skin of the patient with a contact surface of the mobile phone; and
applying, as the contact surface contacts the outer surface, the electrical stimulation signal, from the contact surface to the outer surface such that the electrical stimulation signal passes through the skin to a nerve at a target location within a body of the patient, wherein the electrical stimulation signal is sufficient to modulate the nerve and thereby ameliorate the seizures.

2. The method of claim 1 wherein the seizures are epileptic seizures.

3. The method of claim 1, wherein the contact surface transmits the electrical stimulation signal transcutaneously through the outer surface to a vagus nerve of the patient.

4. The method of claim 1, further comprising:
forecasting at least one of the seizures; and
applying, as the contact surface contacts the outer surface, the electrical stimulation signal from the contact surface through the outer surface to the nerve prior to an onset of the at least one of the seizures to avert the at least one of the seizures.

5. The method of claim 1, further comprising:
prophylactically treating the seizures with a treatment regimen, wherein the treatment regimen comprises continuously applying the electrical signal for a time period from about 30 seconds to about 300 seconds as a single dose and wherein the treatment regimen comprises applying a single dose on a daily basis, wherein the electrical stimulation signal is not applied between a plurality of single doses.

6. The method of claim 5 wherein the treatment regimen comprises applying from 2 to 5 single doses per day.

7. The method of claim 1, wherein the wirelessly transmitting includes downloading a mobile application software onto the mobile phone.

8. The method of claim 7, wherein the mobile application software is the audio file.

9. The method of claim 8 further comprising amplifying the electrical stimulation signal.

10. The method of claim 9, wherein the amplifying is performed within the mobile phone.

11. The method of claim 9, wherein the amplifying includes electrically coupling an amplifier to the mobile phone.

12. The method of claim 1, wherein the outer surface extends along a neck of the patient.

13. The method of claim 1, wherein the electrical stimulation signal comprises bursts of pulses with each of the bursts having a frequency from about 1 to about 100 bursts per second and each of the pulses having a frequency from about 1 to about 20 KHz.

14. The method of claim 1, further comprising wirelessly transmitting data for an electrical stimulation therapy to the mobile phone.

15. The method of claim 14, wherein the wirelessly transmitting data includes downloading a mobile application software program onto the mobile phone.

16. A method comprising:
wirelessly receiving an electrical stimulation signal via a mobile phone, wherein the electrical stimulation signal has a frequency of about 1 Hz to about 100 Hz; and
applying, as a contact surface contacts an outer surface of a skin of a patient diagnosed with seizures, the electrical stimulation signal from the contact surface to the outer surface such that the electrical stimulation signal (1) passes through the skin to a nerve within a body of the patient, (2) modulates the nerve, and (3) ameliorates the seizures, wherein
the electrical stimulation signal is generated by a device remote from the mobile phone.

17. The method of claim 16, wherein the outer surface extends along a neck of the patient.

18. The method of claim 16, wherein the mobile phone comprises a housing encased in a case and has an outer side with the contact surface.

* * * * *